US010761028B2

(12) United States Patent
Raphael et al.

(10) Patent No.: US 10,761,028 B2
(45) Date of Patent: Sep. 1, 2020

(54) DETERMINING EXTRACELLULAR ANALYTE CONCENTRATION WITH NANOPLASMONIC SENSORS

(71) Applicant: The Government of the United States of America, as represented by the Secretary of the Navy, Arlington, VA (US)

(72) Inventors: Marc P. Raphael, Springfield, VA (US); Joseph A. Christodoulides, Alexandria, VA (US); Jeff M. Byers, Fairfax Station, VA (US); James B. Delehanty, Washington, DC (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 484 days.

(21) Appl. No.: 15/186,742

(22) Filed: Jun. 20, 2016

(65) Prior Publication Data

US 2016/0370290 A1    Dec. 22, 2016

Related U.S. Application Data

(60) Provisional application No. 62/181,939, filed on Jun. 19, 2015.

(51) Int. Cl.
| | |
|---|---|
| *G01N 33/48* | (2006.01) |
| *G01N 21/64* | (2006.01) |
| *G01N 33/543* | (2006.01) |
| *G01N 21/552* | (2014.01) |
| *G06G 7/58* | (2006.01) |

(52) U.S. Cl.
CPC ......... *G01N 21/648* (2013.01); *G01N 21/554* (2013.01); *G01N 21/6458* (2013.01); *G01N 33/54373* (2013.01)

(58) Field of Classification Search
None
See application file for complete search history.

(56) References Cited

U.S. PATENT DOCUMENTS

| | | |
|---|---|---|
| 2014/0093977 A1 | 4/2014 | Raphael et al. |
| 2014/0095100 A1 | 4/2014 | Raphael et al. |
| 2014/0273002 A1 | 9/2014 | Raphael et al. |

OTHER PUBLICATIONS

Bailey, et al. "DNA-encoded antibody libraries: A unified platform for multiplexed cell sorting and detection of genes and proteins," *J. Am. Chem. Soc.*, vol. 129(7), pp. 1959-1967 (2007).
Bailey, et al., "Sintered spinel ceramics", Ceram. Bull, vol. 47(11), pp. 1025-1029 (1968).
Beck, et al., "Vascular development: Cellular and molecular regulation," *FASEB J.* vol. 11(5)., pp. 365-373 (1997).
Berezhkovskii, et al., "Cell-to-cell communication: Time and length scales of ligand internalization in cultures of suspended cells," *J. Chem. Phys.*, vol. 128(22), pp. 225102-1-225102-6 (2008).
Bratton, "Coprecipitates yielding MgAl2O4 spinel powders", Ceram. Bull, vol. 48(8), pp. 759-762 (1969).
Costantini, et al., "Fluorescent Proteins in Cellular Organelles: Serious Pitfalls and Some Solutions," *DNA Cell Biol.* vol. 32(11). pp. 622-627(2013).
Dahlin, et al., Specific self-assembly of single lipid vesicles in nanoplasmonic apertures in gold. *Adv. Mater.* vol. 20(8), pp. 1436-1442 (2008).
Endo, et al., "Label-free cell-based assay using localized surface plasmon resonance biosensor," Analytica chimica acta vol. 614.2, pp. 182-189 (2008).
Endo, et al., "Label-free detection of peptide nucleic acid-DNA hybridization using localized surface plasmon resonance based optical biosensor," *Anal. Chem.*, vol. 77(21), pp. 6976-6984 (2005).
Ermakova, et al., "Detection of a Few Metallo-Protein Molecules Using Color Centers in Nanodiamonds," Nano Lett., vol. 13(7), pp. 3305-3309 (2013).
Friedl, et al., "Collective cell migration in morphogenesis, regeneration and cancer," *Nature Reviews Molecular Cell Biology* vol. 10(7), pp. 445-457 (2009).
Haes, et al., "A nanoscale optical biosensor: Sensitivity and selectivity of an approach based on the localized surface plasmon resonance spectroscopy of triangular silver nanoparticles," J. Am. Chem. Soc., vol. 124(35), pp. 10596-10604 (2002).
Han, et al., "Polyfunctional responses by human T cells result from sequential release of cytokines," Proc. Natl. Acad. Sci. U. S. A., vol. 109(5), pp. 1607-1612 (2012).
Heldin, et al., "Mechanism of action and in vivo role of platelet-derived growth factor," *Physiol. Rev.* vol. 79(4), pp. 1283-1316 (1999).
Horowitz, et al., "Electron spin resonance of nitrogen-vacancy centers in optically trapped nanodiamonds," *Proc. Natl. Acad. Sci. U. S. A.* vol. 109(34), pp. 13493-13497 (2012).
Hokazono, et al., "The sintering behavior of spinel powders produced by a homogeneous precipitation technique", Br. Ceram. Trans. & J., vol. 91, pp. 77-79 (1992).

(Continued)

*Primary Examiner* — Eric S Dejong
(74) *Attorney, Agent, or Firm* — US Naval Research Laboratory; Rebecca L. Forman

(57) ABSTRACT

Methods and systems for determining extracellular concentration data of an analyte are disclosed. A method for determining extracellular concentration data of an analyte includes receiving sensor data from one or more arrays of functionalized plasmonic nanostructures on a localized surface plasmon resonance imaging chip in contact with a fluid containing at least one living cell for a plurality of times, determining intensity data for the one or more arrays, determining fractional occupancy based on the intensity data, and determining extracellular concentration data based on the fractional occupancy data. A system for determining extracellular concentration data of an analyte includes a LSPRi chip, a sensor component, an intensity component, a fractional occupancy component, a concentration component, and a processor to implement the components.

14 Claims, 22 Drawing Sheets

(56) References Cited

OTHER PUBLICATIONS

Jonsson, et al., "Supported lipid bilayer formation and lipid-membrane-mediated biorecognition reactions studied with a new nanoplasmonic sensor template," *Nano Lett.* vol. 7(11). pp. 3462-3468 (2007).
Katanic-Popovic, et al., "Spinel formation from coprecipitated gel", Ceram. Int, 17, pp. 49-52 (1991).
Kim, et al., "Synthesis of high purity Yb3+ doped Lu2O3 powder for high power solid state lasers" J. Am. Cer. Soc., 94, pp. 3001-3005 (2011).
Klein, "Figures of merit for high-energy laser-window materials: thermal lensing and thermal stresses", SPIE, pp. 640308-1-640308-16 (2007).
Kolitz, et al., "Measurement and Modeling of Signaling at the Single-Cell Level," *Biochemistry* vol. 51(38), pp. 7433-7443 (2012).
Letterio et al., "Regulation of immune responses by TGF-beta," *Annu. Rev. Immunol.* 16, pp. 137-161(1998).
Li, et al., "Synthesis of Mg—Al spinel powder via precipitation using ammonium bicarbonate as the precipitant", Journal of the European Ceramic Society 21, pp. 139-148 (2001).
Lo, et al., "Monitoring of DNA-protein interaction with single gold nanoparticles by localized scattering plasmon resonance spectroscopy," *Methods*, vol. 64(3), pp. 331-337 (2013).
Mayer, et al., "A single molecule immunoassay by localized surface plasmon resonance," *Nanotechnology,* vol. 21(25) pp. 1-8 (2010).
Monine, et al., "Ligand accumulation in autocrine cell cultures," *Biophys. J.*, vol. 88(4), pp. 2384-2390 (2005).
Nusz, et al., "Label-free plasmonic detection of biomolecular binding by a single gold nanorod," *Anal. Chem.* vol. 80(4), pp. 984-989 (2008).
Oh, et al., "Integrated Nanoplasmonic Sensing for Cellular Functional Immunoanalysis Using Human Blood," *ACS Nano* vol. 8(3), pp. 2667-2676 (2014).
Raphael, et al., "Quantitative LSPR Imaging for Biosensing with Single Nanostructure Resolution," Biophysical J. (104), pp. 30-36 (2013).
Raphael, et al., "A New Methodology for Quantitative LSPR Biosensing and Imaging," Anal. Chem. 84, pp. 1367-1373 (2012).
Raphael, et al., "Quantitative Imaging of Protein Secretions from Single Cells in Real Time," Biophysical J. (105), pp. 602-608 (2013).
Risau, et al., "Vasculogenesis," *Annu. Rev. Cell. Dev. Biol.* 11, pp. 73-91 (1995).
Sepulveda, et al., "LSPR-based nanobiosensors," *Nano Today* vol. 4(3), pp. 244-251 (2009).
Shankaran, et al., "Oscillatory dynamics of the extracellular signal-regulated kinase pathway," *Curr. Opin. Genet. Dev.* 20(6), pp. 650-655 (2010).
Shirasaki, et al., "Real-time single-cell imaging of protein secretion," *Scientific Reports* 4, pp. 1-8 (2014).
Villalobos, et al., "Analysis of scattering sites in transparent magnesium aluminate spinel" Cera. Eng. Sci. Proc., 26, pp. 293-298 (2005).
Werner "Regulation of wound healing by growth factors and cytokines," *Physiol. Rev.* vol. 83(3), pp. 835-870 (2003).
Wiedenmann, et al., "Fluorescent Proteins for Live Cell Imaging: Opportunities, Limitations, and Challenges," *Iubmb Life* vol. 61(11), pp. 1029-1042 (2009).

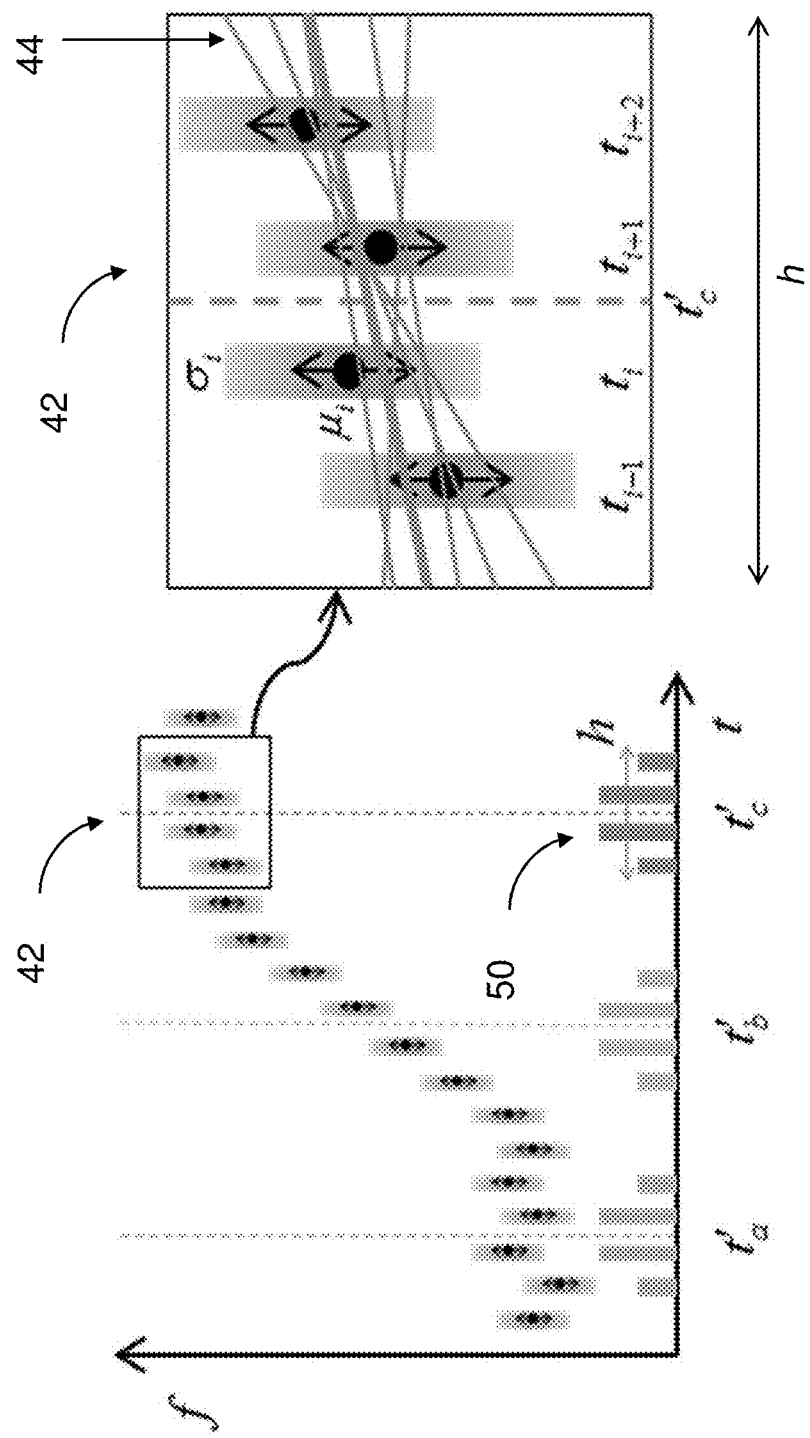

DETERMINING EXTRACELLULAR ANALYTE CONCENTRATION WITH NANOPLASMONIC SENSORS

This application claims the benefit of U.S. Provisional Application No. 62/181,939, filed on Jun. 19, 2015 by Marc P. Raphael et al., entitled IMAGING EXTRACELLULAR PROTEIN CONCENTRATION WITH NANOPLASMONIC SENSORS, the disclosure of which is incorporated herein by reference, in its entirety.

BACKGROUND

Aspects of the exemplary embodiment relate to detection of analytes in a fluid and find particular application in connection with the detection of extracellular proteins using nanoplasmonic sensors.

From bacterium to eukaryote, a cell's fate is directly tied to its local chemical environment. The measurement of external protein concentrations and gradients by membrane bound receptors is useful in the study of cell differentiation, motility and proliferation. Such dependencies have been deduced by introducing artificial gradients to cell cultures. However, direct measurements of the spatio-temporal concentrations of analytes, which cells themselves produce via secretion, have remained elusive.

One roadblock has been the lack of an assay that can measure extracellular protein concentrations in real time without disrupting the signaling pathways of interest. This real time, non-invasive requirement severely limits the techniques that can be employed, including common fluorescent labeling methods. For example, while fluorescent fusion proteins have been useful in the study of intracellular protein measurements, the technique does not lend itself to extracellular signaling. A tag, such as green fluorescent protein (GFP) tag of about 27 kDa, for example, may compromise the labeled protein's ability to navigate the complexities of the secretory pathway (Wiedenmann et al., "Fluorescent Proteins for Live Cell Imaging: Opportunities, Limitations, and Challenges," *Iubmb Life* 61(11):1029-1042 (2009); Costantini, et al., "Fluorescent Proteins in Cellular Organelles: Serious Pitfalls and Some Solutions," *DNA Cell Biol.* 32(11):622-627 (2013)).

Even if the proteins are successfully secreted, the result is a diffuse fluorescent glow outside the cell which is difficult to quantify. Fluorescently-labeled antibodies used for immunosandwich assays have been successfully introduced outside of live cells to measure secretions (Bailey, et al., "DNA-encoded antibody libraries: A unified platform for multiplexed cell sorting and detection of genes and proteins," *J. Am. Chem. Soc.* 129(7):1959-1967 (2007); Han, et al., "Polyfunctional responses by human T cells result from sequential release of cytokines," *Proc. Natl. Acad. Sci. U.S.A.* 109(5):1607-1612 (2012); Shirasaki, et al., "Real-time single-cell imaging of protein secretion," *Scientific Reports* 4 (2014)). However, the addition of these relatively large probes (typically 150 kDa) is an impediment to downstream signaling and the techniques typically involve isolating individual cells. In both examples, the ability to establish causal relationships between secreted protein concentrations and cell fate, whether the signaling be autocrine, paracrine or endocrine in nature, is hampered by the probes themselves.

Solid-state nanosensors have the potential to overcome this impasse. Probes such as nanodiamonds and metallic nanostructures are biocompatible, do not suffer from photobleaching and, advantageous from the protein secretion perspective, are label-free techniques. Nanodiamond sensors are highly sensitive magnetic field detectors resulting from nitrogen vacancies, which makes the technique particularly applicable to detecting metalloproteins (Horowitz, et al., "Electron spin resonance of nitrogen-vacancy centers in optically trapped nanodiamonds," *Proc. Natl. Acad. Sci. USA.* 109(34):13493-13497 (2012); Ermakova, et al., "Detection of a Few Metallo-Protein Molecules Using Color Centers in Nanodiamonds," *Nano Lett.* 13(7):3305-3309 (2013)). Metallic nanoparticles exhibit a localized surface plasmon resonance (LSPR) which is sensitive to changes in the local refractive index of the surrounding medium. Their surfaces can be biofunctionalized for the detection of proteins, lipids, and DNA in cell-free environments (Sepulveda, et al., "LSPR-based nanobiosensors," *Nano Today* 4(3):244-251 (2009); Mayer, et al., "A single molecule immunoassay by localized surface plasmon resonance," *Nanotechnology* 21(25) (2010); Haes, et al., "A nanoscale optical biosensor: Sensitivity and selectivity of an approach based on the localized surface plasmon resonance spectroscopy of triangular silver nanoparticles," *J. Am. Chem. Soc.* 124(35): 10596-10604 (2002); Nusz, et al., "Label-free plasmonic detection of biomolecular binding by a single gold nanorod," *Anal. Chem.* 80(4):984-989 (2008); Jonsson et al., "Supported lipid bilayer formation and lipid-membrane-mediated biorecognition reactions studied with a new nanoplasmonic sensor template," *Nano Lett.* 7(11):3462-3468 (2007); Dahlin, et al., "Specific self-assembly of single lipid vesicles in nanoplasmonic apertures in gold," *Adv. Mater.* 20(8):1436-1422 (2008); Endo, et al., "Label-free detection of peptide nucleic acid-DNA hybridization using localized surface plasmon resonance based optical biosensor," *Anal. Chem.* 77(21):6976-6984 (2005); Lo, et al., "Monitoring of DNA-protein interaction with single gold nanoparticles by localized scattering plasmon resonance spectroscopy," *Methods* 64(3):331-337 (2013)). In addition, LSPR optical configurations are readily integrated with standard wide-field microscopy setups which have enabled the detection of protein secretions in the presence of thousands of cells, as well as real-time single cell secretions (Oh, et al. "Integrated Nanoplasmonic Sensing for Cellular Functional Immunoanalysis Using Human Blood," *ACS Nano* 8(3):2667-2676 (2014); Endo et al., "Label-free cell-based assay using localized surface plasmon resonance biosensor," *Anal. Chim. Acta* 614(2):182-189 (2008); Raphael et al., Quantitative Imaging of Protein Secretions from Single Cells in Real Time. *Biophys. J.* 105(3):602-608 (2013)). However, measuring extracellular protein concentrations in both space and time, for modeling and quantifying of signaling pathways, has remained a challenge (Kolitz, et al., "Measurement and Modeling of Signaling at the Single-Cell Level," *Biochemistry* 51(38):7433-7443 (2012)).

Additionally, methods using spectrometry-based techniques are severely restrictive in that they only allow for a single array's response to be quantified, and the spectrometer requires a lot of light and significant exposure time, which could be harmful to live cells.

Thus, it would be desirable to have a method and system for measuring extracellular analyte concentrations in space and time, without the need for use of fluorescent tagging and without the need to use a spectrometer.

INCORPORATION BY REFERENCE

The following references, the disclosures of which are incorporated herein by reference in their entireties, are mentioned.

U.S. Pub. No. 2014/0273002, published Sep. 18, 2014, entitled NANOSPLASMONIC IMAGING TECHNIQUE FOR THE SPATIO-TEMPORAL MAPPING OF SINGLE CELL SECRETIONS IN REAL TIME by Marc P. Raphael, et al.

U.S. Pub. No. 2014/0095100, published Apr. 3, 2014, entitled CALIBRATING SINGLE PLASMONIC NANOSTRUCTURES FOR QUANTITATIVE BIOSENSING by Marc P. Raphael, et al.

U.S. Pub. No. 2014/0093977, published Apr. 3, 2014, entitled LIGHT MICROSCOPY CHIPS AND DATA ANALYSIS METHODOLOGY FOR QUANTITATIVE LOCALIZED SURFACE PLASMON RESONANCE (LSPR) BIOSENSING AND IMAGING by Marc P. Raphael, et al.

BRIEF DESCRIPTION

In accordance with one aspect of the exemplary embodiment, a method for determining extracellular concentrations of an analyte includes receiving sensor data from one or more arrays of functionalized plasmonic nanostructures on a localized surface plasmon resonance imaging (LSPRi) chip in contact with a fluid containing at least one living cell for a plurality of times. Intensity data is determined for the nanostructures, based on the sensor data for each of the plurality of times. fractional occupancy data is determined for the nanostructures, based on the intensity data for each of the plurality of times. Extracellular concentration data of the analyte is determined, based on the fractional occupancy data for each of the plurality of times.

One or more of the steps of the method may be performed with a processor.

In accordance with another aspect of the method, the method may further comprise determining movement of the analyte in the fluid from the extracellular concentration data by mapping the extracellular concentration data of the analyte for the LSPRi chip.

In accordance with another aspect of the exemplary embodiment, a computer-implemented system for determining extracellular concentrations of an analyte includes a localized surface plasmon resonance imaging (LSPRi) chip, a sensor component for receiving sensor data for a plurality of times, an intensity component that determines image intensity data based on the sensor data for the plurality of times, a fractional occupancy component that determines fractional occupancy data based on the intensity data for each of the plurality of times, and a concentration component that determines extracellular concentration data based on the fractional occupancy data for each of the plurality of times. The LSPRi chip includes a substrate and one or more arrays of functionalized plasmonic nanostructures formed on the substrate. Each array is in contact with a fluid containing at least one living cell. A processor implements the components.

In accordance with another aspect of the exemplary embodiment, a method of determining extracellular concentrations of an analyte in a fluid includes providing at least one array of functionalized plasmonic nanostructures on a localized surface plasmon resonance imaging (LSPRi) chip in contact with a fluid containing at least one living cell. For each of a plurality of times, sensor data is received from one or more of the arrays of functionalized plasmonic nanostructures. Fractional occupancy data is determined for the nanostructures based on the sensor data for each of the plurality of times. Extracellular concentration of the analyte is spatially and temporally mapped, based on the fractional occupancy data.

BRIEF DESCRIPTION OF THE DRAWINGS

FIGS. 9-11 schematically illustrate data analysis for determining concentration form fractional occupancy, where FIG. 9 illustrates subsampling of fractional occupancy over time; FIG. 10 illustrates an enlarged portion of the plot of FIG. 9, and FIG. 11 is a plot illustrating each linear model as a point in a plane;

DETAILED DESCRIPTION

Methods and systems for measuring extracellular concentrations of an analyte are disclosed wherein single cell secretions may be imaged over time and spatial distance from one or more biological cells. The technique is useful for determining the flow of analytes, such as proteins, lipids, and DNA, in a liquid medium.

In embodiments disclosed herein, arrays of gold plasmonic nanostructures are used for real-time imaging of secreted protein concentrations. The inference of concentration from nanoplasmonic imagery is assisted by two techniques. First, when normalized, LSPR imagery (LSPRi) can be used to determine the fraction of active surface ligands bound to the analyte (fractional occupancy). Second, to calculate concentration, an analysis approach is used which is based on temporal filtering that utilizes the LSPRi-determined fractional occupancy and reaction rate constants as inputs. Applying this approach to the spatio-temporal mapping of secreted antibody concentrations from hybridoma cells, single cell secretions can be imaged with a time resolution of 15 seconds over a spatial range extending 130 µm from the center of the cell. Sensing arrays located next to individual cells resolved steady-state concentrations between 0.2 and 1.3 nM. Burst-like secretions can also be measured in which the transient concentration reaches as high as 56 nM over the course of several minutes and then dissipates. The ability to measure secreted concentrations with high spatial and temporal resolution has applicability to numerous analytes and cell types.

Figure 1:
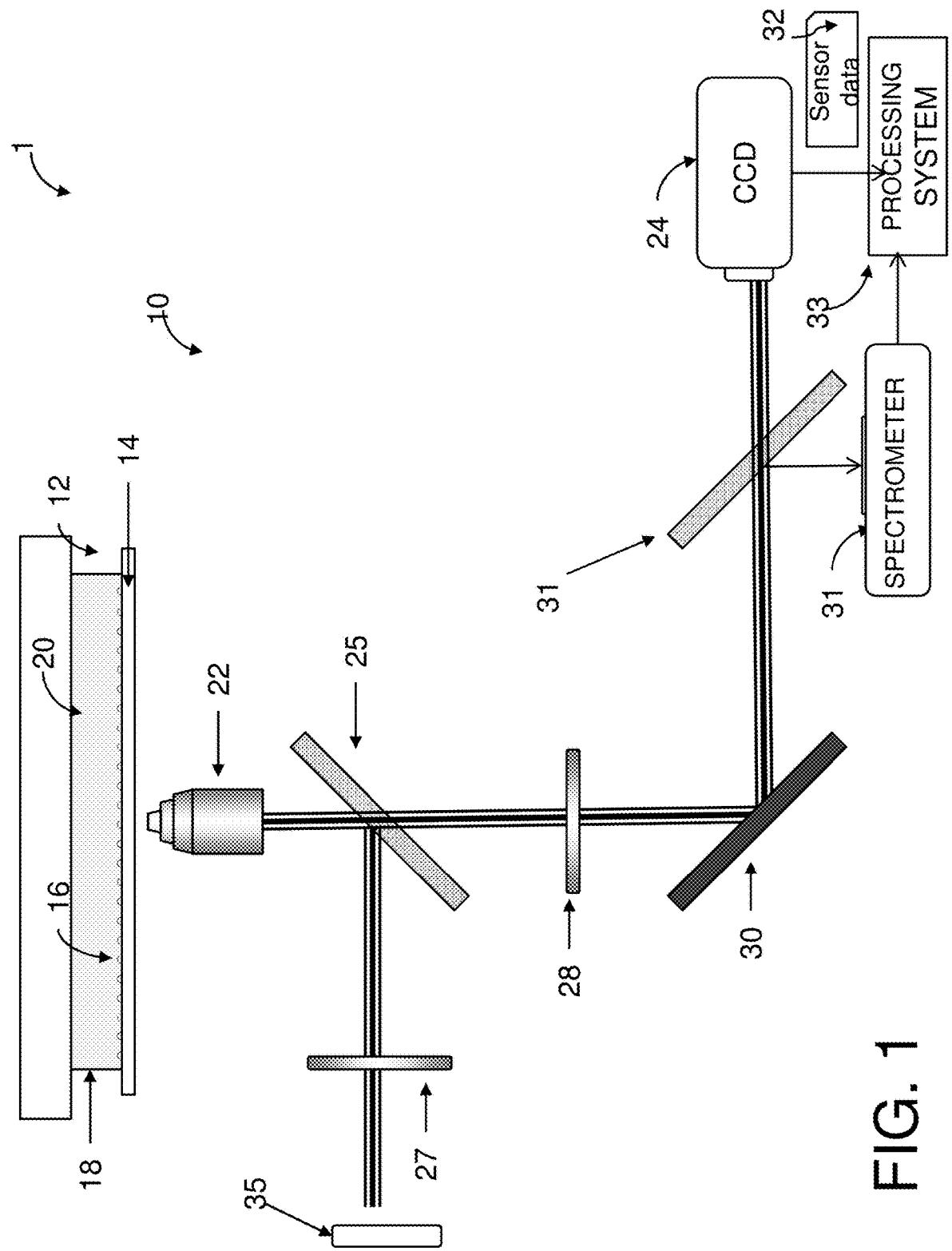
FIG. 1 is a schematic diagram of a portion of an apparatus used to measure extracellular concentrations of an analyte according to one aspect of the exemplary embodiment.

With reference to FIG. 1, an illustration of a detection system 1 used to measure extracellular concentrations of an analyte in a liquid medium according to one aspect of the exemplary embodiment is shown. The detection system 1 includes an apparatus 10, which includes: an LSPRi chip 12, which includes a light-transmitting substrate 14, such as a glass coverslip, which is patterned with a plurality of nanostructures 16, which may be arranged in one or more arrays. The glass coverslip may be of the type conventionally used in a standard light microscope.

A chamber 18, mounted on the substrate 14, holds a liquid medium 20, which is in contact with the nanostructures 16. The liquid medium may contains one or more living cells. An objective lens 22 is positioned adjacent the substrate to receive emissions from the nanostructures passing therethrough. A charge coupled device (CCD) 24, such as a CCD camera, is positioned to receive inputs from the lens. In particular embodiments, the apparatus 10 may include one or more of: beam splitters 25, 26, a linear polarizer 27, a crossed linear polarizer 28, and a mirror 30. Other detection devices, such as a spectrometer 31, may optionally be included. In use, the excitation light from a visible light source 35, such as a halogen lamp, passes through the linear polarizer 27 and illuminates the arrays 34 through the objective lens 22. Photons emitted by the nanostructure are collected by the objective lens 22, passed through the crossed linear polarizer 28 and reflected by mirror 30 to CCD camera (labeled CCD). Optionally, a beam splitter 31, intermediate the mirror 30 and CCD, allows some of the energy (reflected light) to enter the spectrometer 31. Alternatively, the spectrometer 31 is omitted from the system 1. Sensor data 32 from the detection device(s) 24, 31 are sent to a processing system 33, which is described in greater detail with reference to FIG. 5.

Figure 2:
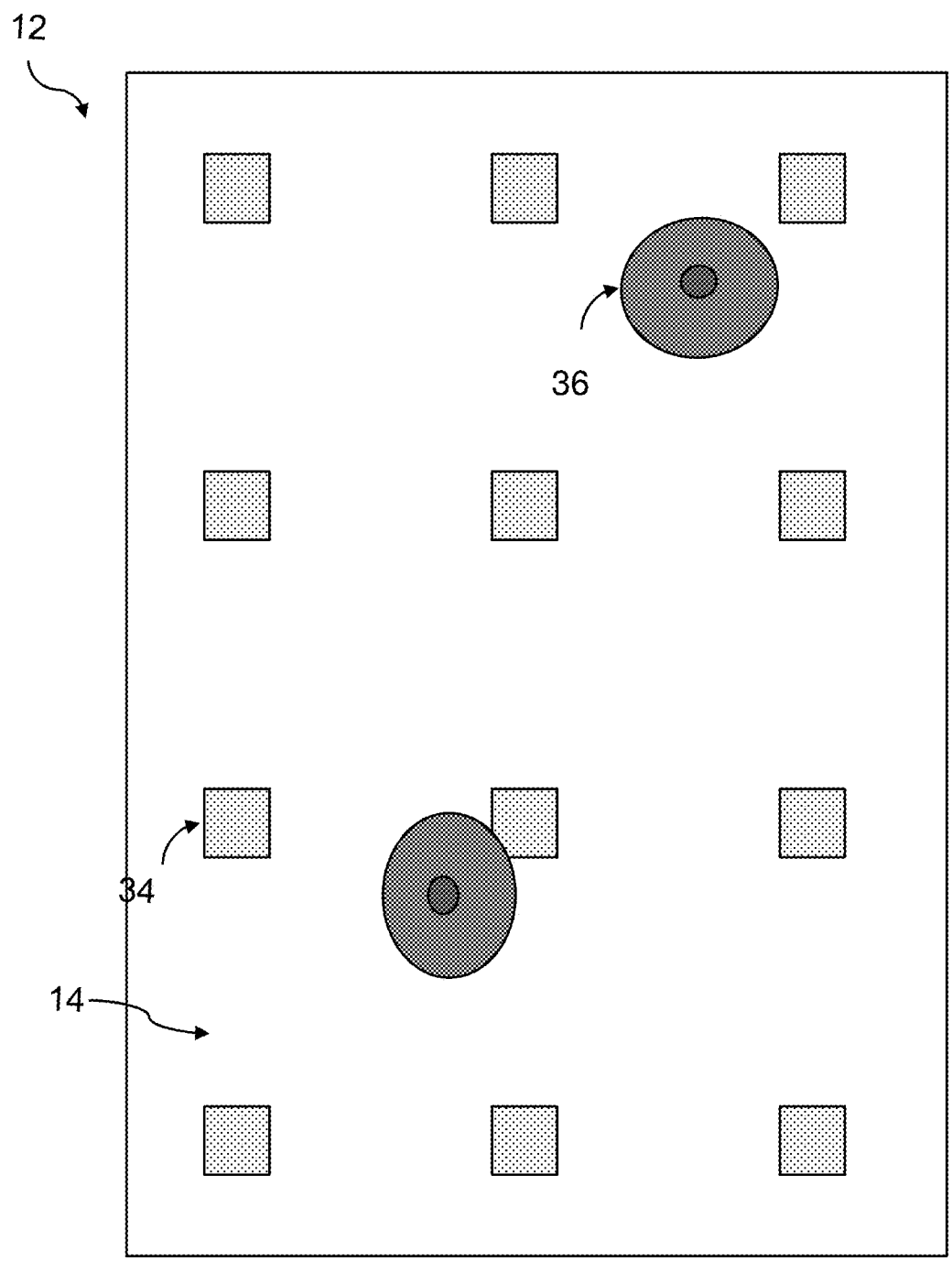
FIG. 2 is top plan view of a LSPRi chip according to another aspect of the exemplary embodiment.

With reference to FIG. 2, a top view of an exemplary LSPRi chip 12 is shown. The LSPRi chip 12 includes one or more arrays 34 of nanostructures. In the embodiment illustrated in FIG. 2, twelve arrays 34 of plasmonic nanostructures 16 are shown. In particular embodiments, the coverslip 14 is patterned via electron beam lithography to incorporate arrays 34 of plasmonic nanostructures 16, which may be formed predominantly of gold. One or more live cells 36 are located in the liquid medium, in proximity to the coverslip 14 and the arrays 34 of nanostructures 16.

With reference one again to FIG. 1, the arrays 34 are illuminated with a source 35 of visible illumination, such as a 100 W halogen lamp. The polarizers 26, 28 may be used to minimize background contributions from light scattered by the glass substrate.

Figure 3:
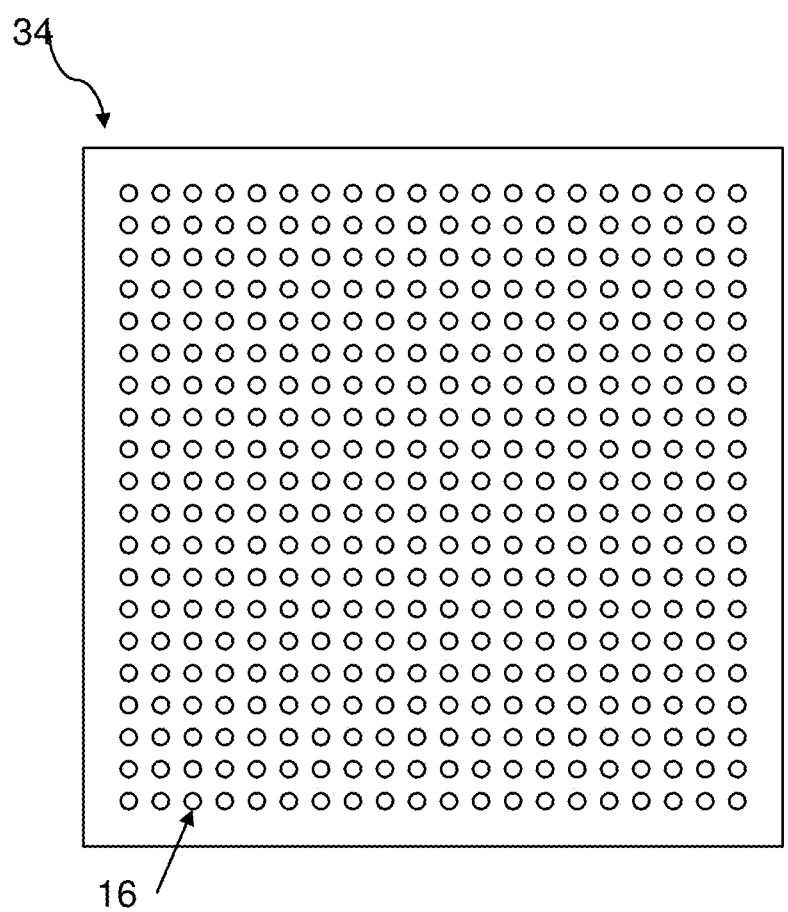
FIG. 3 is a top plan view of an array of nanostructures in the LSPR chip of FIG. 2.

With reference also to FIG. 3, a single array 34 of nanostructures 16 is shown. Each nanostructure 16 may be at least 10 nm, or at least 20 nm, or up to 200 nm, or up to 100 nm, or up to 250 nm, in diameter, and at least 20 nm, or at least 50 nm, or up to 500 nm, or up to 200 nm, in height. In specific embodiments, the nanostructures 16 may be 70-80, e.g., 75 nm in diameter and 60-100, e.g., 80 nm in height.

The nanostructures 16 may be arranged in different patterns, such as an n×m array 34, where each of n and m is at least 5, such as up to 50. For example, as shown in FIG. 3, the nanostructures 16 may be arranged in a 20×20 array 34. In particular embodiments, the nanostructures 16 may be spaced from 200 to 1000 nm apart, center-to-center, which thus defines the pitch range. The nanostructures 16 may have thus a pitch of 300-500 nm. The arrays 34 may have a pitch of at least 5 µm, or at least 20 µm, such as at least 30 µm, or up to 100 µm, or up to 40 µm, e.g., 33 µm as measured from their respective centers.

The arrays 34 may have a resonance peak centered at 250-800 nm. In some embodiments, the arrays 34 may have a resonance peak centered at about 635 nm in aqueous media.

Figure 4:
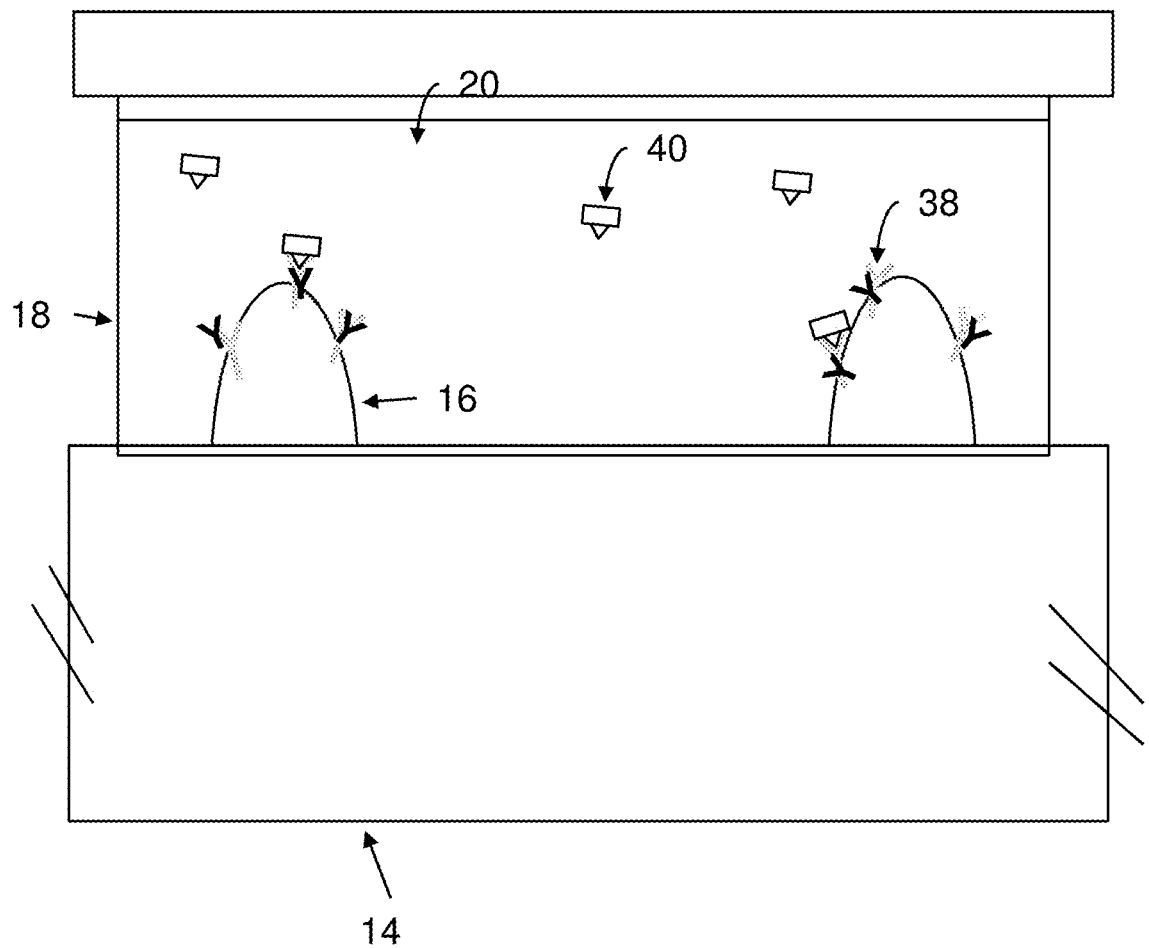
FIG. 4 is a side sectional view of functionalized nanostructures in the LSPR chip of FIG. 2.

Methods for forming the arrays of nanostructures are described, for example, in above-mentioned U.S. Pub. Nos. 2014/0273002, 2014/0095100, and 2014/0093977, incorporated herein by reference With reference to FIG. 4, an enlarged side sectional view of a portion of the LSPRi chip 12 is shown, with two functionalized nanoplasmonic structures 16. The nanostructures 16 may be functionalized with ligands 38 that are able to bind a specific target analyte 40 in the liquid medium. For example, the nanostructures 16 may be biologically functionalized by first applying a two-component self-assembled monolayer of first and second thiols in a 3:1 ratio. The majority (first) thiol component may be terminated with polyethylene glycol to prevent non-specific binding while the minority (second) component terminates with an amine group (or other functional binding group) for covalent ligand attachment.

The analyte 40 may be a protein, such as an antibody, secreted by one or more cells 36 contained within the fluid 20 of the chamber 18. Analyte 40 binding to the ligands 38 causes a perturbation in the local index of refraction of the plasmonic nanostructures 16, which is manifested as a spectral red shift and increase in intensity. When imaged by the CCD camera, the arrays 34 are observed to brighten with increasing spectral shift (i.e., increased binding). A known analyte 40 (e.g., commercially obtained in high purity) may be used to normalize the spectral response of the arrays 34 of functionalized nanostructures 16, e.g., after testing In particular embodiments, the configuration of the apparatus 10 integrates with traditional cell microscopy techniques, such as fluorescence and/or brightfield imaging, which may be accessible by the automated switching of a filter cube (not shown).

Figure 5:
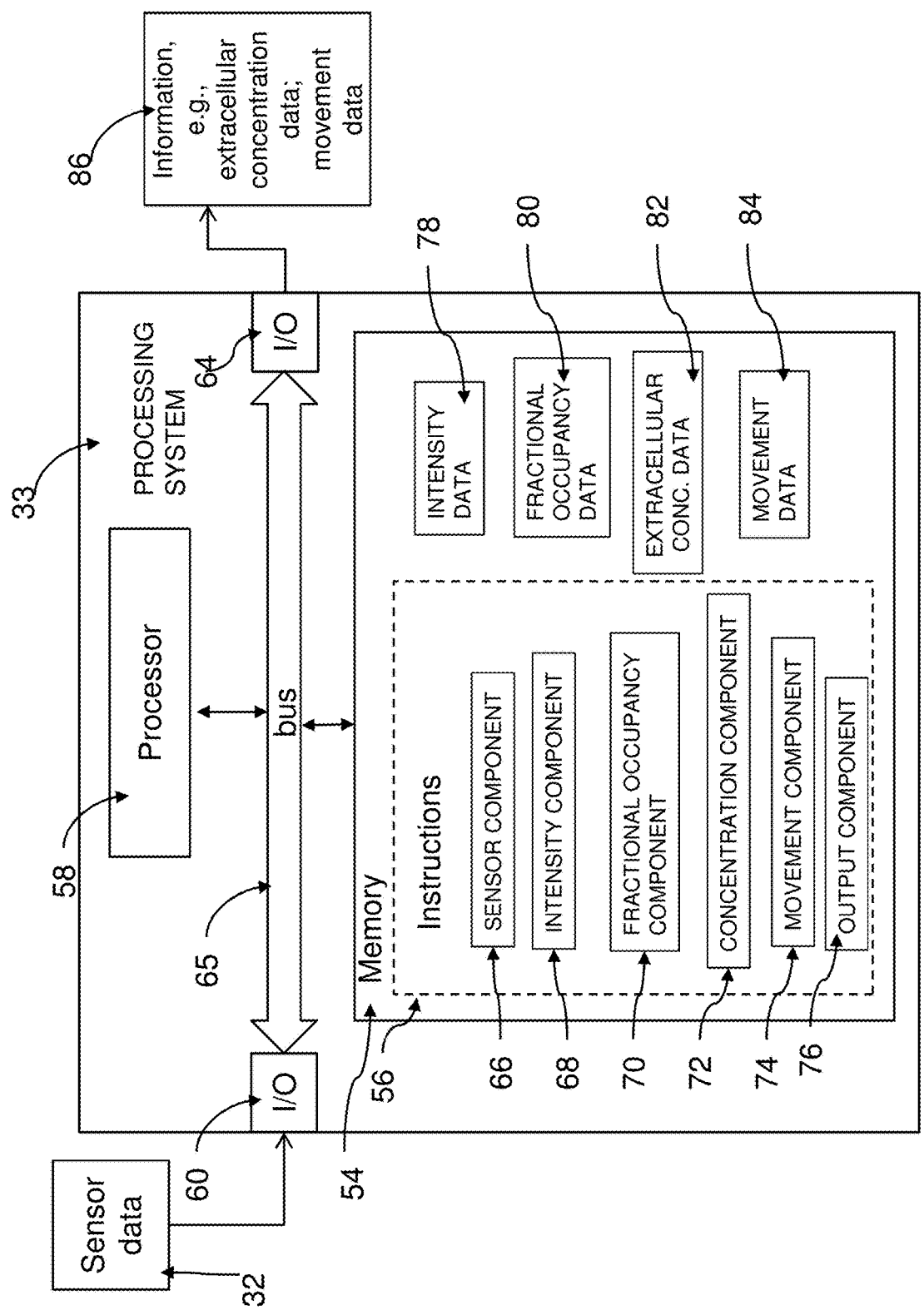
FIG. 5 is a functional block diagram of a computer-implemented system for measuring extracellular concentrations of an analyte in a liquid medium according to another aspect of the exemplary embodiment.

With reference to FIG. 5, a functional block diagram of a computer-implemented sensor data processing system 33 for determining extracellular concentration data of an analyte is shown. The illustrated computer system 33 includes memory 54 which stores software instructions 56 for performing the method illustrated in FIG. 6 and a processor 58 in communication with the memory for executing the instructions 56. The system 33 also includes one or more input/output (I/O) devices 60, 64, such as a network interface and a user input output interface. The I/O interface 64 may communicate with one or more displays, for displaying information to users, and a user input device, such as a keyboard, or touch or writable screen, and/or a cursor control device, such as mouse, trackball, or the like, for inputting text and for communicating user input information and command selections to the processor device 58. I/O interface 60 receives sensor data 32 from the detection device(s) 24, 31. The various hardware components 54, 58, 60, 64 of the processing system 33 may all be connected by a data/control bus 65.

The data processing system 33 may include one or more computing devices, such as a PC, such as a desktop, a laptop, palmtop computer, portable digital assistant (PDA), server computer, cellular telephone, tablet computer, pager, combination thereof, or other computing device capable of executing instructions for performing the exemplary method.

The memory 54 may represent any type of non-transitory computer readable medium such as random access memory (RAM), read only memory (ROM), magnetic disk or tape, optical disk, flash memory, or holographic memory. In one embodiment, the memory 54 comprises a combination of random access memory and read only memory. In some embodiments, the processor 58 and memory 54 may be combined in a single chip. Memory 54 stores instructions for performing the exemplary method as well as the processed data.

The network interface 60, 64 allows the computer to communicate with other devices via a wired or wireless link, e.g., a computer network, such as a local area network (LAN) or wide area network (WAN), or the internet, and may comprise a modulator/demodulator (MODEM), a router, a cable, and/or Ethernet port.

The digital processor device 58 can be variously embodied, such as by a single-core processor, a dual-core processor (or more generally by a multiple-core processor), a digital processor and cooperating math co-processor, a digital controller, or the like. The digital processor 58, in addition to executing instructions 56, may also control the operation of the processing system 33.

The illustrated instructions 56 include a sensor component 66, an intensity component 68, a fractional occupancy component 70, a concentration component 72, a movement component 74, and an output component 76.

Briefly, the sensor component 66 receives sensor data 32 from the one or more arrays of nanostructures for each of a plurality of times (or time windows, such as at least 5, 10, 20, or more times). The intensity component 68 determines intensity data 78 for the one or more arrays of nanostructures, based on the sensor data 32 for each of the plurality of times. The fractional occupancy component 70 determines fractional occupancy data 80 for the arrays of nanostructures, based on the intensity data 78, for each of the plurality of times. The concentration component 72 determines extracellular concentration data 82 of the analyte, based on the fractional occupancy data 80, for each of the plurality of times.

In some particular embodiments, the system 52 comprises a localized surface plasmon resonance imaging (LSPRi) chip 76, which includes a glass coverslip and one or more arrays of functionalized plasmonic nanostructures patterned on the glass coverslip in contact with a fluid containing at least one living cell. In particular embodiments, The sensor component 66 receives sensor data from inputs 60 such as the one or more arrays of nanostructures on the LSPRi chip 76 for a plurality of times. In particular embodiments, the sensor data may comprise images brightfield and/or LSPRi images of the LSPRi chip 76 taken by additional inputs 60 such as a charge-coupled device 76.

The intensity component 68 determines intensity data for the one or more arrays of nanostructures based on the sensor data received by the sensor component 66. In particular embodiments, the intensity component 68 determines intensity data for each of the arrays and for each of the plurality of times. According to some embodiments, at least one of the one or more arrays is selected as a control array to be subtracted out from the experimental arrays. In further embodiments, the intensity data is determined by normalizing the average intensity of each of the one or more arrays of nanostructures for a plurality of times.

The fractional occupancy component 70 determines fractional occupancy data for the one or more arrays of nanostructures based on the intensity data determined by the intensity component 68. In particular embodiments, the fractional occupancy component 70 determines fractional occupancy data for each of the plurality of times. According to exemplary embodiments, a saturating amount of analyte is added to the LSPRi chip at the end of the experiment, and a relationship between the intensity data and fractional occupancy is used to determine the fractional occupancy data.

The concentration component 72 determines extracellular concentration data 82 for the one or more arrays of nanostructures based on the fractional occupancy data determined by the fractional occupancy component 70. In particular embodiments, the concentration component 72 determines concentration data 82 for each of the plurality of times. In some embodiments, the concentration component 72 subsamples the fractional occupancy data 80 over the plurality of times to determine the concentration data 82 for each of the plurality of times. In particular embodiments, the concentration data 82 is determined as a probability distribution of potential concentrations for each of the one or more arrays of nanostructures. In exemplary embodiments, the concentration data 82 is determined as described in the method above.

The movement component 74 determines movement data 84, which indicates the predicted movement of the analyte 40 in the fluid 20, based on the extracellular concentration data 82. This is achieved by mapping the extracellular concentration data for each of the one or more arrays of nanostructures over the plurality of times to provide spatiotemporal concentration data.

The output component 76 outputs information 86, which may include one or more of: the concentration data 82, movement data 84, and/or information based thereon.

In one embodiment, the system 1 does not include a spectrometer. In this embodiment, the sensor component 66 does not receive sensor data 32 from a spectrometer, and the intensity component 68 and fractional occupancy component 70 determine the intensity data and fractional occupancy data without data from a spectrometer. In another embodiment, the system 1 may be integrated with traditional cell microscopy techniques such as fluorescence and/or brightfield imaging, which are accessible by the automated switching of a filter cube. In some embodiments, transmitted light imaging and/or fluorescence imaging may be performed simultaneously with the LSPR imaging.

The term "software," as used herein, is intended to encompass any collection or set of instructions executable by a computer or other digital system so as to configure the computer or other digital system to perform the task that is the intent of the software. The term "software" as used herein is intended to encompass such instructions stored in storage medium such as RAM, a hard disk, optical disk, or so forth, and is also intended to encompass so-called "firmware" that is software stored on a ROM or so forth. Such software may be organized in various ways, and may include software components organized as libraries, Internet-based programs stored on a remote server or so forth, source code, interpretive code, object code, directly executable code, and so forth. It is contemplated that the software may invoke system-level code or calls to other software residing on a server or other location to perform certain functions.

Figure 6:
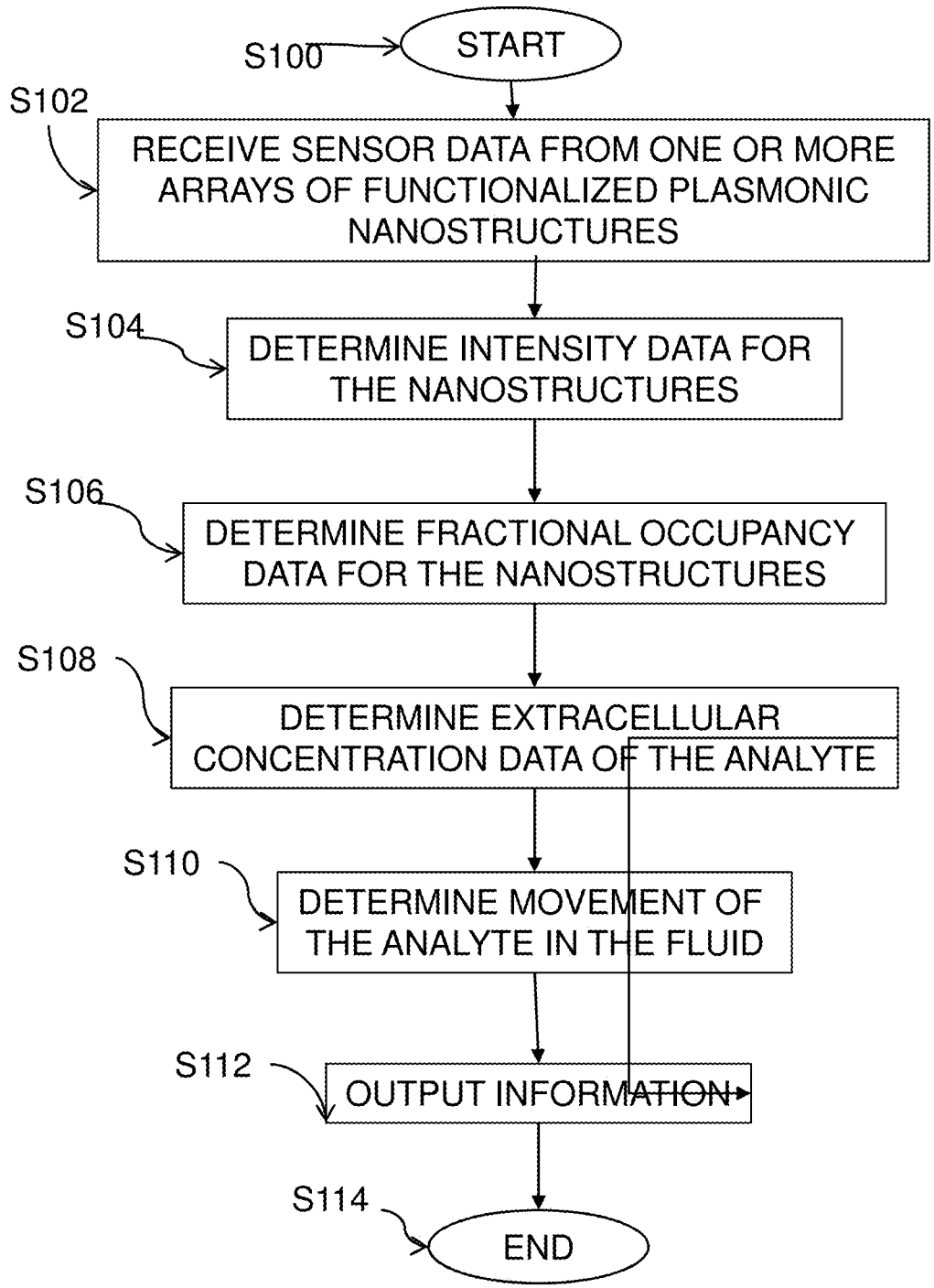
FIG. 6 is a flow chart illustrating a method for measuring extracellular concentrations of an analyte in accordance with another aspect of the exemplary embodiment.

With reference to FIG. 6, a computer-implemented method for determining extracellular concentrations of an analyte is illustrated. The method starts at S100.

At S102, sensor data 32 is received by the processing system 33 from the one or more arrays 34 of functionalized plasmonic nanostructures 16. In particular embodiments, the sensor data may be received using a charge coupled device 24, such as a CCD camera. In other embodiments, the sensor data may comprise additional forms of sensor data, such as sensor data from fluorescence and brightfield imaging techniques. In exemplary embodiments, the sensor data is not received using an optical spectrometer.

At S104, intensity data 78 for the arrays 34 of nanostructures 16 is determined.

At S106, fractional occupancy data 80 for the arrays 34 of nanostructures 16 is determined based on the intensity data 78. Fractional occupancy, denoted f, represents the fraction of the arrays 34 of nanostructures 16 that have an analyte 40 molecule bound to them.

At S108, extracellular concentration data 82 of the analyte is determined, based on the fractional occupancy data 80 of the arrays 34 of nanostructures 16. In order to determine analyte concentration from the sensor data, the qualitative feature of array 34 brightening on the CCD camera 24 is quantified in terms of the fraction occupancy data.

Optionally, at S110, the movement of an extracellular analyte may be determined spatially and temporally based on the extracellular concentration data 82. In particular embodiments, extracellular concentration data is determined for one or more of the arrays 34 of nanostructures 16. Based on the determined extracellular concentration data, the probability distributions of the concentration for each array 34 may be mapped in both time and space, e.g., for a sequence of 5, 10, 20, 100, or more time intervals of at least 1, 5, 10, or more seconds, or up to 100 or 1000 seconds, over a spatial range extending at least 1, 10, 20, 50, or 100 µm, or more, from the center of the cell.

At S112, information is output, such as the concentration data, movement data, information based thereon, or a combination thereof.

The method ends at S114.

The method illustrated in FIG. 6 may be implemented in a computer program product that may be executed on a computer. The computer program product may comprise a non-transitory computer-readable recording medium on which a control program is recorded (stored), such as a disk, hard drive, or the like. Common forms of non-transitory computer-readable media include, for example, floppy disks, flexible disks, hard disks, magnetic tape, or any other magnetic storage medium, CD-ROM, DVD, or any other optical medium, a RAM, a PROM, an EPROM, a FLASH-EPROM, or other memory chip or cartridge, or any other non-transitory medium from which a computer can read and use. The computer program product may be integral with the computer, (for example, an internal hard drive of RAM), or may be separate (for example, an external hard drive operatively connected with the computer), or may be separate and accessed via a digital data network such as a local area network (LAN) or the Internet (for example, as a redundant array of inexpensive or independent disks (RAID) or other network server storage that is indirectly accessed by the computer, via a digital network).

Alternatively, the method may be implemented in transitory media, such as a transmittable carrier wave in which the control program is embodied as a data signal using transmission media, such as acoustic or light waves, such as those generated during radio wave and infrared data communications, and the like.

The exemplary method may be implemented on one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphics card CPU (GPU), or PAL, or the like. In general, any device, capable of implementing a finite state machine that is in turn capable of implementing the flowchart shown in FIG. 6, can be used to implement the method for determining extracellular concentrations of an analyte. As will be appreciated, while the steps of the method may all be computer implemented, in some embodiments one or more of the steps may be at least partially performed manually. As will also be appreciated, the steps of the method need not all proceed in the order illustrated and fewer, more, or different steps may be performed.

Further details of the system and method will now be provided.

In the exemplary embodiment, image intensity data 78 is determined (at S104) based on the sensor data 32 received from the charge coupled device 24, without the use of a spectrometer. To determine the intensity data 78, the mean intensity I(t), at time t of each array 34, as measured by the charge coupled device 24, is normalized, e.g., by dividing the difference between I(t) and $I_0$ by a constant value to obtain a normalized intensity value at time t:

$$I_N(t) = (I(t) - I_0)/(I_f - I_0),$$

where $I_0$ and $I_f$ are the initial and saturated array 34 intensity values, respectively.

When a conventional spectrometer is used, the fractional occupancy shows a non-linear relationship with image intensity making it difficult to quantify. It has been discovered, however, that there is a linear relationship between the normalized image intensity data received from the sensors using a CCD camera 24 and the fractional occupancy data. Thus, it is possible to determine fractional occupancy data without the use of a spectrometer. It has been observed that this relationship holds whether the analyte is, for example, a 150 kDa antibody, such as anti-c-myc or 60 kDA neutravidin proteins binding to a biotinylated surface. However, if the CCD camera 24 has a strong wavelength-dependence on its quantum efficiency (QE) in the vicinity of the resonance, non-linearities tend to be introduced. The size and pitch (i.e., space between) the nanostructures 16 can be designed so that the resonance is located in a relatively flat region of the camera's 24 QE response while also being red-shifted from excitation wavelengths used for common fluorescent tags, such as GFP and red fluorescent protein (RFP).

Figure 7:
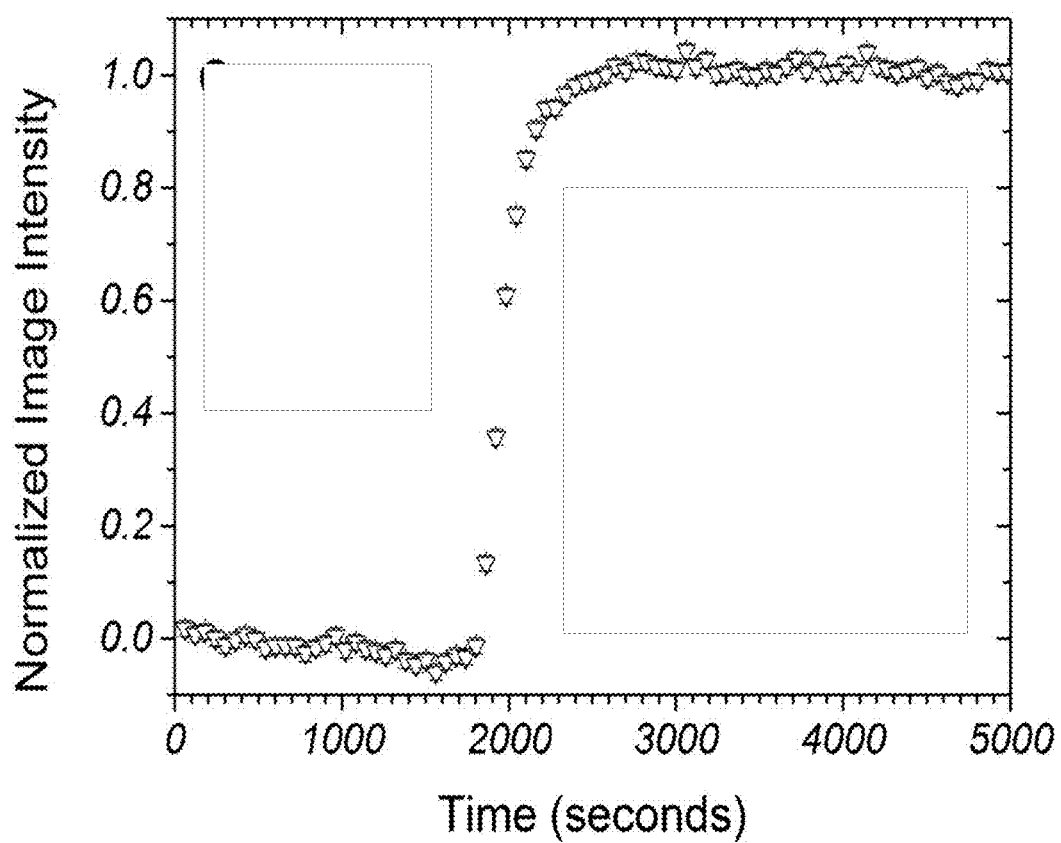
FIG. 7 is a graph of normalized image intensity vs time for the exemplary CCD camera.

FIG. 7 shows a plot of the normalized image intensity of a CCD camera using the apparatus of FIG. 1 using a 400 nanostructure array of gold nanostructures with a pitch of 500 nm excited with a halogen lamp. The single 20×20 array is aligned with the optical fiber.

Figure 8:
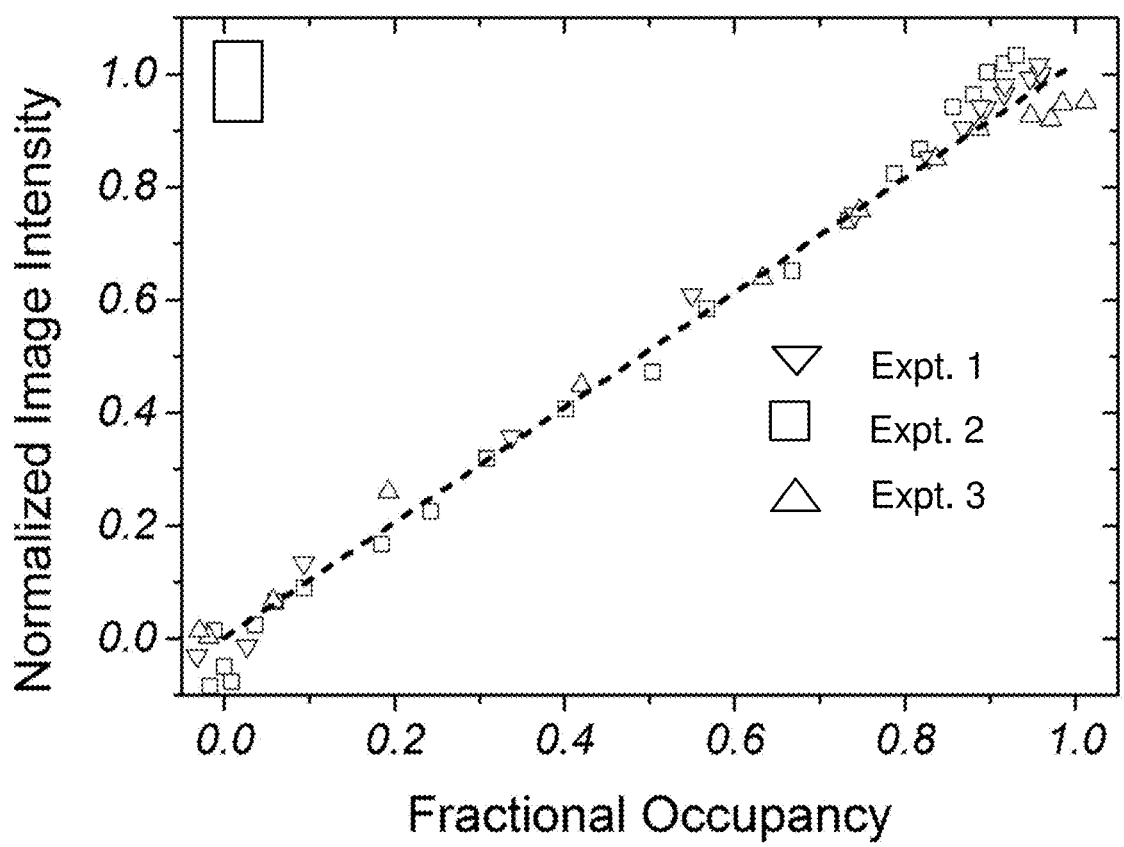
FIG. 8 is a graph of normalized image intensity vs fractional occupancy obtained in three experiments.

FIG. 8 shows the normalized image intensity versus the spectrally-determined fractional occupancy obtained in three separate experiments, illustrating the linear relationship between them. Experiments 1 and 2 use anti-c-myc monoclonal antibodies binding to a c-myc functional array in phosphate buffered saline (PBS) and serum-free media, respectively, and Experiment 3 uses neutravidin binding for biotinylated nanostructures.

Fractional occupancy data 80 computed at S106 may include estimated (mean) fractional occupancy $\mu_i$ for an array, and its variance (e.g., standard deviation) $\sigma_i$, for each of M images at time $t_i$, where i in an index referencing the data collected from the i-th image of M images, where M may be the number of arrays 34. This processed LSPRi data may be denoted D={$t_i$, $\mu_i$, $\sigma_i$|i=1, . . . , M}.

In particular embodiments, the fractional occupancy data is determined for one or more of the arrays 34 of functionalized nanostructures 16.

Based on the fractional occupancy data, the law of mass action can be applied to determine analyte concentration, C, using the formula:

$$\dot{f} = k_a C \cdot (1-f) - k_d f,$$

where $\dot{f}$ is the time-derivative of the fractional occupancy $\mu_i$, $k_a$ is the association rate constant for the functionalized nanostructures 16, and $k_d$ is the disassociation rate constant for the functionalized nanostructures 16.

For this approach, f and $\dot{f}$, together with their related uncertainties, are first jointly determined. In particular embodiments, the step of determining the extracellular concentration data of the analyte includes first subsampling the fractional occupancy data using a temporal filter 42 over the plurality of times, and calculating the time-derivative fractional occupancy data, as illustrated schematically in FIGS. 9-11.

With reference to FIG. 9, fractional occupancy data is plotted over a plurality of times. A time window or temporal filter 42 is shown. The fractional occupancy data within the window is subsampled. The time window 42 moves along the time-axis subsampling the fractional occupancy data within each window 42. The time window 42 shown has a center at time $t_c'$, and a width h, which represents a time interval.

The time-derivative fractional occupancy may be determined based on the subsampled fractional occupancy data. In some embodiments, one or more local linear models 44 are calculated for each of the instances of subsampling based on the time window 42. Specifically, a model mean fractional occupancy $\bar{f}$ and model mean time-derivative fractional occupancy $\bar{\dot{f}}$, are determined, based on the local linear models 44 calculated for each subsample of fractional occupancy data.

FIG. 10 is an enlarged view of the samples around $t_c'$ of FIG. 9. The vertical bars represent the standard deviation $\sigma_i$, for each fractional occupancy data points, $\mu_i$. A plurality of local linear models 44 that could fit the data (given the predicted deviation $\sigma_i$) are shown for the time window 42, centered at time $t_c'$ and with a width h.

Given the normal distribution ($\mu_i$, $\sigma_i$) for the fractional occupancy at each $t_i$, the probability of each of the different local linear models 44 explaining the data can be determined and a most probable one is selected. Each time window or temporal filter 42 gives a weight $w_i$ to the subsampled data by increasing the variance of data over the range of h. Specifically, the fractional occupancy data further from the center $t_c'$ of the time window 42 contributes less to the local linear models 44 than the fractional occupancy data closer to the center $t_c'$.

In particular embodiments, the probability of different local linear models fitting the data can be expressed and determined using a negative-log likelihood formula:

$$L = -\ln p(f, \dot{f} \mid t, h; D) = \sum_{i=1}^{n} \left( w(t_i \mid t, h) \cdot \frac{[f + \dot{f} \cdot (t_i - t) - \mu_i]^2}{2\sigma_i^2} + \text{optionally terms independent of } f \text{ and } \dot{f} \right)$$

where $w(t_i|t, h)$ are the weights assigned to $t_i$ by the temporal filter 42, and i is an index referencing a plurality of data points from 1 to n data points.

Various functions for $w(t_i|t, h)$ defining the temporal filter 42 may be used. In some embodiments, the functional defining the temporal filter 42 may be a generic Gaussian profile, schematically shown as bar graphs 50 in FIG. 9. For example, the temporal filter may be given by the equation:

$$w(t_i|t,h) = e^{-(t_i-t)^2/2h^2}$$

where t is the center of the time window 42, and h is the width of the time window 42.

In other embodiments, a different symmetric, location-scale function (e.g., Lorentzian, Epanechnikov) can be chosen as the filter. The chosen function should be positive and have a maximum value of one.

The width, h, is a free parameter that can be fixed for the entire data set or adaptively set for each center t. The statistical property of bias-variance tradeoff is one consideration in selecting h, because a narrow width (small h) provides a very local estimate of f and $\dot{f}$ but a high variance due to the small number of noisy samples. A wider width (large h) samples more data and reduces the variance, but the bias will increase if non-linearities in f and $\dot{f}$ emerge on large time-scales.

In particular embodiments, the probability distribution, L, may be determined and expressed as a bivariate normal distribution with five parameters: $\bar{f}$, $\bar{\dot{f}}$, $\rho_{xx}$, $\rho_{xy}$, and $\rho_{yy}$, wherein $\bar{f}$ and $\bar{\dot{f}}$ are mean model parameters determined by the local linear models 44, and $\rho_{xx}$, $\rho_{xy}$, and $\rho_{yy}$ are the elements of the inverse of the covariance matrix.

Using Laplace's method, a Taylor series expansion of L to the second order at the maximum value of L may be used to express L as a bivariate normal distribution:

$$L = \text{const.} + \frac{1}{2} \begin{pmatrix} f - \bar{f} \\ \dot{f} - \bar{\dot{f}} \end{pmatrix}^T \sum\nolimits^{-1} \begin{pmatrix} f - \bar{f} \\ \dot{f} - \bar{\dot{f}} \end{pmatrix},$$

$$\sum\nolimits^{-1} = \begin{pmatrix} \sigma_{xx} & \sigma_{xy} \\ \sigma_{xy} & \sigma_{yy} \end{pmatrix}^{-1} = \begin{pmatrix} \rho_{xx} & \rho_{xy} \\ \rho_{xy} & \rho_{yy} \end{pmatrix}$$

wherein: T is the transpose, $\Sigma$ is a 2-by-2 covariance matrix and the $\sigma$ terms are the covariance matrix elements defined by the second order terms of the Taylor series expansion.

Taking the first derivatives of L with respect to f and $\dot{f}$, and setting these to zero yields a set of equations for the location, $\bar{f}$ and $\bar{\dot{f}}$, of the maximum value of L:

$$\frac{\partial L}{\partial f}\bigg|_{f=\bar{f},\dot{f}=\bar{\dot{f}}} = \sum_{i=1}^{n} w_i \cdot \frac{\bar{f} + \bar{\dot{f}} \cdot (t_i - t) - \mu_i}{\sigma_i^2} = 0$$

$$\frac{\partial L}{\partial \dot{f}}\bigg|_{f=\bar{f},\dot{f}=\bar{\dot{f}}} = \sum_{i=1}^{n} w_i \cdot (t_i - t) \cdot \frac{\bar{f} + \bar{\dot{f}} \cdot (t_i - t) - \mu_i}{\sigma_i^2} = 0$$

Taking the second derivatives of L provides the equations for the inverse covariance matrix:

$$\rho_{xx} = \frac{\partial^2 L}{\partial f^2} = \sum_{i=1}^{M} \frac{w_i}{\sigma_i^2},$$

$$\rho_{xy} = \frac{\partial^2 L}{\partial f \partial \dot{f}} = \sum_{i=1}^{M} \frac{w_i}{\sigma_i^2} \cdot (t_i - t),$$

and $$\rho_{yy} = \frac{\partial^2 L}{\partial \dot{f}^2} = \sum_{i=1}^{M} \frac{w_i}{\sigma_i^2} \cdot (t_i - t)^2$$

In particular embodiments, because no further terms depend on f and $\dot{f}$, the parameterization of L as a bivariate normal distribution is exact for linear models.

The second derivatives can be used to re-write the previous equations as:

$$\rho_{xx}\bar{f} + \rho_{xy}\bar{\dot{f}} = \underbrace{\sum_{i=1}^{M} \frac{w_i}{\sigma_i^2}\mu_i}_{\equiv a}$$

$$\rho_{xy}\bar{f} + \rho_{yy}\bar{\dot{f}} = \underbrace{\sum_{i=1}^{M} \frac{w_i}{\sigma_i^2}\mu_i \cdot (t_i - t)}_{\equiv b}$$

and solved to obtain:

$$\bar{f} = \frac{\rho_{yy}a - \rho_{xy}b}{\rho_{xx}\rho_{yy} - \rho_{xy}^2}$$

and $$\bar{\dot{f}} = \frac{\rho_{yy}b - \rho_{xy}a}{\rho_{xx}\rho_{yy} - \rho_{xy}^2}$$

where a and b are sums over the weighted mean and the weighted mean times its time difference, respectively.

The bivariate normal probability distribution for p(f, $\dot{f}$|t, h; D) can then be expressed as:

$$p(f, \dot{f} \mid t, h; D) = \frac{(\rho_{xx}\rho_{yy} - \rho_{xy}^2)^{1/2}}{2\pi} \cdot \exp\left[-\frac{1}{2}\begin{pmatrix}f - \bar{f}\\\dot{f} - \bar{\dot{f}}\end{pmatrix}^T \begin{pmatrix}\rho_{xx} & \rho_{xy}\\\rho_{xy} & \rho_{yy}\end{pmatrix}\begin{pmatrix}f - \bar{f}\\\dot{f} - \bar{\dot{f}}\end{pmatrix}\right]$$

All of the parameters are therefore expressed in terms of the weights at time t, $w(t_i|t, h)$, and the processed LSPRi data, $D = \{t_i, \mu_i, \sigma_i, i=1, \ldots, M\}$.

In particular embodiments, the extracellular concentrations of an analyte may be determined as a probability distribution of the concentration at time t:

$$p(c \mid t, h; D) = \frac{1}{Z}\int_0^1 df \int_{-\infty}^{\infty} d\dot{f}\, p(c \mid f, \dot{f}) p(f, \dot{f} \mid t, h; D)$$

where c is a dimensionless concentration defined by $c = C/K_D$, $K_D = k_d/k_a$, Z is a normalization function, which may be defined by $Z = \int_0^{\infty} dc\, p(c|t, h; D)$, and p(f, $\dot{f}$|t, h; D) is a bivariate normal distribution as described above.

By integrating over the model parameters f and $\dot{f}$, the probability distribution of the concentration c, at each time t, of interest can be determined, assuming a particular kinetic binding model represented by p(c|f, $\dot{f}$).

The probability p(c|f, $\dot{f}$) represents the relationship of the fractional occupancy to the concentration and is, therefore, the contribution from the kinetic binding model. A deterministic equation that relates these quantities based on the Law of Mass Action can be expressed as:

$$c = \gamma(f, \dot{f}),$$

where $$\gamma(f, \dot{f}) \equiv \frac{k_d^{-1}\dot{f} - f}{1 - f}$$

Therefore, p(c|f, $\dot{f}$) can be expressed as:

$$p(c|f,\dot{f}) \propto \delta(c - \gamma(f,\dot{f}))$$

and the two-dimensional integral can be reduced to a line integral:

$$p(c \mid t, h; D) = \frac{1}{Z}\int_0^1 df \int_{-\infty}^{\infty} d\dot{f}\, \delta(c - \gamma(f, \dot{f})) p(f, \dot{f} \mid t, h; D)$$

$$= \frac{1}{Z}\sqrt{1 + (1+c)^2} \int_0^1 df\, p(f, \dot{f}(c, f) \mid t, h; D)$$

where $\dot{f}(c, f) = k_d c - k_d(1+c) \cdot f$.

Finally, the integral can be numerically determined at each time t over enough values of c to estimate the width of the probability distribution and, thus, the associated error.

The probability distribution of c, p(c|t, h; D), can be expressed as:

$$p(c \mid t, h; D) = \frac{1}{Z(t, h; D)}\sqrt{1 + (1+c)^2} \cdot e^{-\frac{1}{2}G + \frac{B^2}{2A}} \int_0^1 df\, e^{-\frac{A}{2}(f - \frac{B}{A})^2}$$

where the coefficients A, B, and G, are functions of the concentration and the parameters of the bivariate normal distribution, but are independent of f:

$$A(c)=\rho_{xx}-2k_d\rho_{xy}(1+c)+k_d^2\rho_{yy}(1+c)^2$$

$$B(c)=\rho_{xx}\tilde{f}+k_d\rho_{xy}(k_d^{-1}\tilde{f}(1+c))-k_d^2\rho_{yy}(k_d^{-1}\tilde{f}-c)\cdot(1+c)$$

$$G(c)=\rho_{xx}\tilde{f}^2+2k_d\rho_{xy}\tilde{f}(k_d^{-1}\tilde{f}-c)+2k_d^2\rho_{yy}(k_d^{-1}\tilde{f}-c)^2$$

Each of the coefficients A, B, and G are dimensionless.

Figure 11:
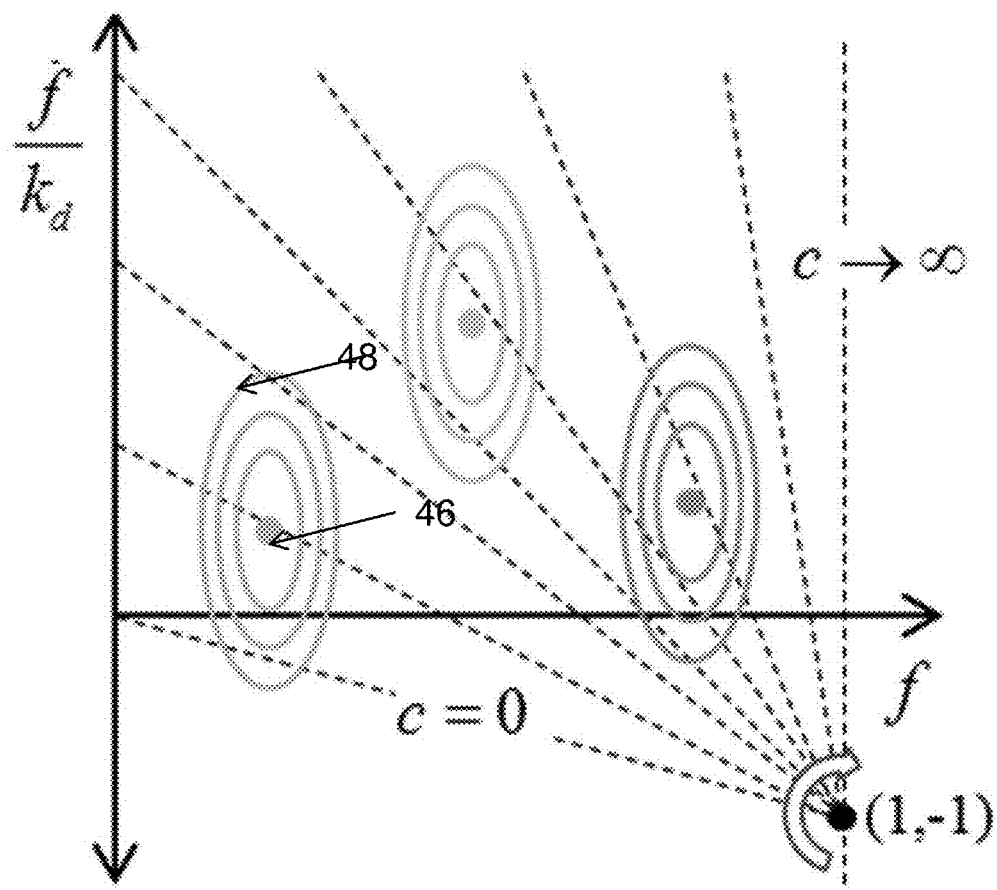

With reference to FIG. 11, this integration is illustrated. Each local linear model 44 is a point in the f–f plane 46. All possible local linear models 44 are summarized by the probability distribution p(f, f|t, h; D), a bivariate normal distribution (depicted as elliptical contours) 48 with five parameters: the mean value ($\bar{f}$, $\bar{\dot{f}}$), and the entries ($\sigma_{xx}$, $\sigma_{xy}$, $\sigma_{yy}$) in the 2-by-2 covariance matrix $\Sigma$. Using the law of mass action for the kinetic binding model, a concentration can be assigned to each point (f, f). The probability of a particular concentration c, at a time t, is determined by integrating p(f, f|t, h; D) along the lines of constant concentration shown as the dashed lines radiating from the point (1, −1). The constant value for the concentration of each line increases in the clockwise direction, and each line integral is successively evaluated to determine p(c|t, h; D) for all c.

The Gaussian integral over the interval 0 to 1 can be solved in terms of error functions, erf(x). In other embodiments, the integral is determined using numerical integration. For example, the probability distribution of extracellular concentrations is solved using the integral function in MATLAB, which employs globally adaptive quadrature. The probability distribution of the concentrations can be determined by repeating the integral on an evenly-space logarithmic grid of values of c ranging from $10^{-4}$ to $10^5$ for each of a plurality of times t. For example, the calculation may be repeated for at least 100, or at least 500, or at least 1000, values of c.

In particular embodiments, the normalization function Z is computed by non-adaptive numerical integration using only the values of c selected.

The resulting probability distributions p(c|t, h; D) may be summed over sub-intervals of c to produce confidence intervals at each time t, typically at 5% and 95% of the total probability.

Various applications of the system and method are contemplated. In a co-culture environment the label free nature of the measurements enables absolute concentration and concentration gradient measurements from one cell type to be correlated to the response of another, which is useful for determining causal relations between the secretions and cellular responses such as motility and division. At the individual cell level, the technique can be used to identify polarized secretions useful in developmental biology and cell migration. In addition, the fact that the technique integrates with commonly used techniques in fluorescence microscopy allows for both label and label-free investigations of the cells. Printing applications, such as ink jet and dip-pen lithography can be utilized to expand the functionality for multiplexing applications capable of quantifying a variety of secreted proteins in parallel.

Without intending to limit the scope of the exemplary embodiment, the following examples illustrate the application of the system and method.

EXAMPLES

1. Fabrication and Functionalization of Plasmonic Nanostructures

Arrays of nanostructures were patterned onto No. 1.5 glass coverslips by spinning a bilayer resist structure consisting of polymethyl methacrylate and ethyl lactate methyl methacrylate copolymer with thicknesses of 180 nm and 250 nm respectively. The resist was electron-beam patterned using doses of 300 µC/cm² and subsequently developed for one minute in a 2:1 solution of isopropyl alcohol:methyl isobutyl ketone. A 5 nm layer of Ti followed by 70 nm of Au was deposited with a Temescal electron-beam evaporator. The bilayer resist was then lifted off by soaking in acetone for 4 hours.

Radio frequency (RF) plasma ashing (40 W) with 300 mTorr of a 5% hydrogen, 95% argon mixture was used to clean the glass and gold surfaces on the chips. The gold nanostructures were functionalized in a two-component ethanolic-based thiol bath (0.5 mM), containing a 3:1 ratio of $SH-(CH_2)_8-EG_3-OH$ to $SH-(CH_2)_{11}-EG_3-NH_2$ for 18 hours, where EG stands for ethylene glycol monomer. The amine terminus was reacted with a 10 mg/mL solution of the heterobifunctional crosslinker sulfo-N-succinimidyl-4-formylbenzamide (Solulink) in phosphate-buffered saline (PBS) at pH 7.4, followed by a hydrazine functionalized c-myc peptide conjugation (Solulink) in PBS buffer at pH 6.0 according to the manufacturer's instructions. For biotin-neutravidin studies, 0.3 mM of sulfo-NHS-biotin (Thermo) in PBS was drop-coated onto the chip for 30 min. Chips were rinsed with DDW and dried with nitrogen gas. Commercially available monoclonal anti-c-myc antibodies (Sigma) were used for normalizing array response at the end of each experiment.

2. Microscopy Setup and Drift Correction

Halogen lamp light was first passed through a 594 long-pass filter and then the Koehler illumination train of an inverted microscope (Zeiss AxioObserver) before following the light path described in FIG. 1. The objective used was a 63×, 1.46 numerical aperture oil-immersion objective. For spectral measurements, a 600 µm diameter optical fiber was used to collect the scattered light from a single array and detected with thermoelectrically-cooled, CCD-based spectrophotometer (Ocean Optics QE65000) at an integration time of 1 s. A thermoelectrically-cooled CCD camera (Hamamatsu ORCA R2) with integration times between 200 and 250 ms was used for imagery. A heated stage and temperature controlled enclosure kept the stage temperature at 37.0±0.04° C. (Zeiss). Humidity and $CO_2$ were regulated at 98% and 5%, respectively, by flowing a gas-air mixture though a heated water bottle and into the enclosure. In plane drift was corrected for with image alignment software (Zeiss Axiovision) while the focus was stabilized using an integrated hardware focus correction device (Zeiss Definite Focus).

3. Cell Culturing

Clone 9E10 Hybridoma cells (ATCC) were cultured in complete growth medium RPMI-1640 supplemented with 10% fetal bovine serum and 1% antibiotic/antimycotic in a humidified tissue culture incubator at 37° C. under a 5% $CO_2$ atmosphere. Cells were maintained at a density of $3-5\times10^5$ cells/mL by performing passaging every two days which maintained viability at 90-95%. Prior to LSPRi studies, the cells were pelleted by centrifugation (900 rcf×5 min) and washed twice with RPMI-1640 SFM for the removal of secreted antibodies and serum. For imaging, 75 µL of $0.5-2\times10^6$ cells/mL cell solution was manually injected into the fluidics chamber. Cell surface density was controlled by allowing cells to settle on the surface for 5 to 10 min and then microfluidically flowing SFM to remove those still in solution.

4. Data Analysis

All analysis was conducted using the Matlab 2013b environment according to exemplary embodiments of the methods and systems described herein.

a. Simulated Measurements

Figure 12:
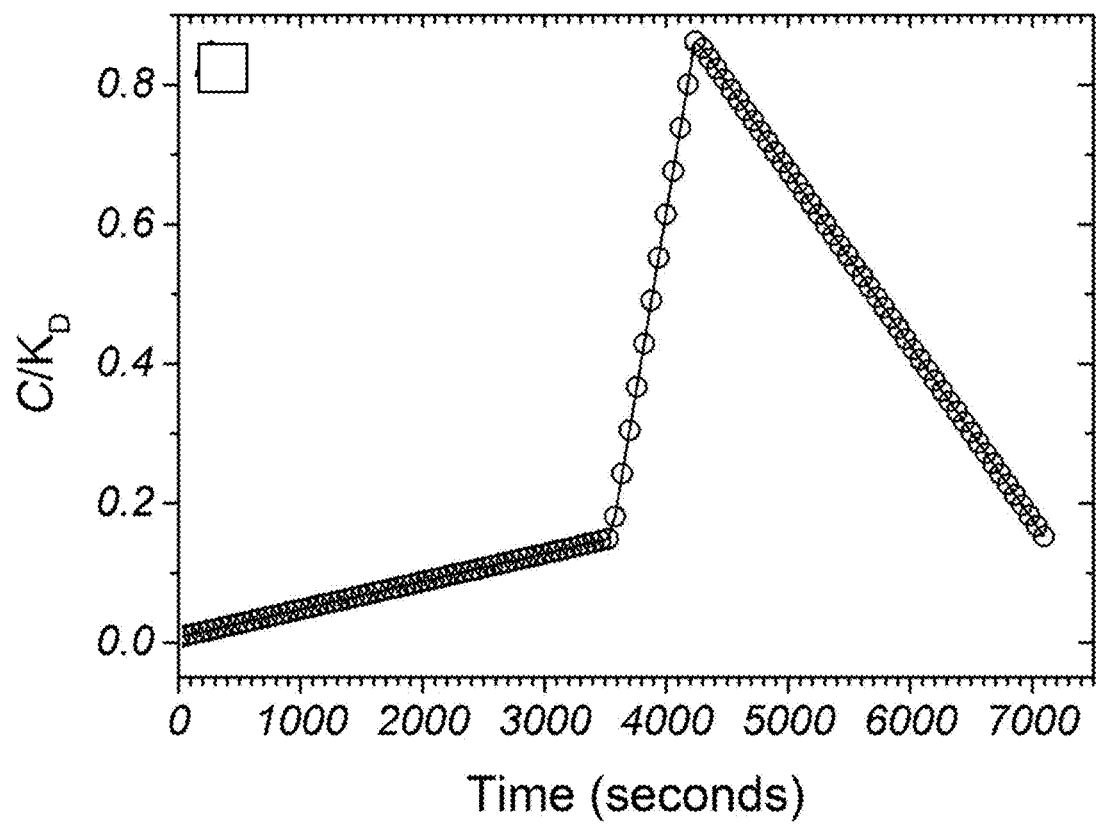
FIG. 12 is a graph of a piece-wise function of three simulated time-dependent concentration scenarios: a gradual increase; a sharp increase; and a sharp decline, vs time in determining extracellular concentrations from simulated data.
Figure 13:
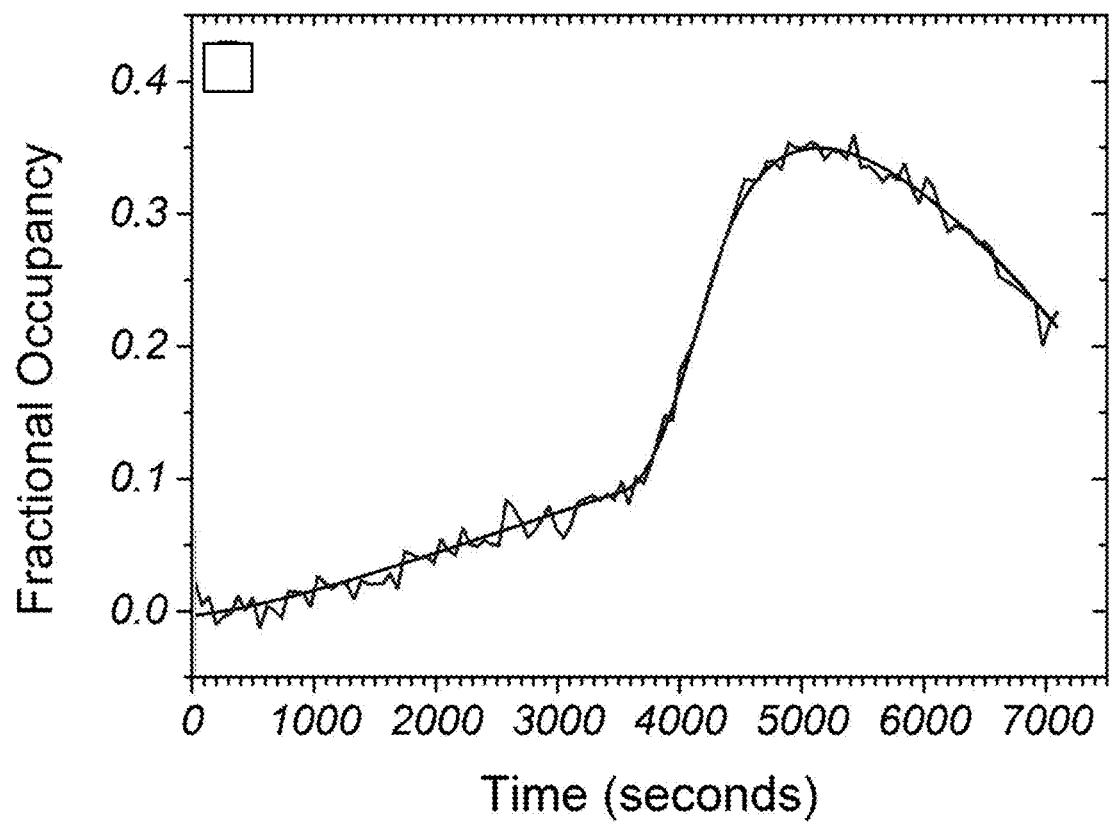
FIG. 13 is a graph of fractional occupancy vs time in determining extracellular concentrations from simulated data, with simulated Gaussian noise.
Figure 14:
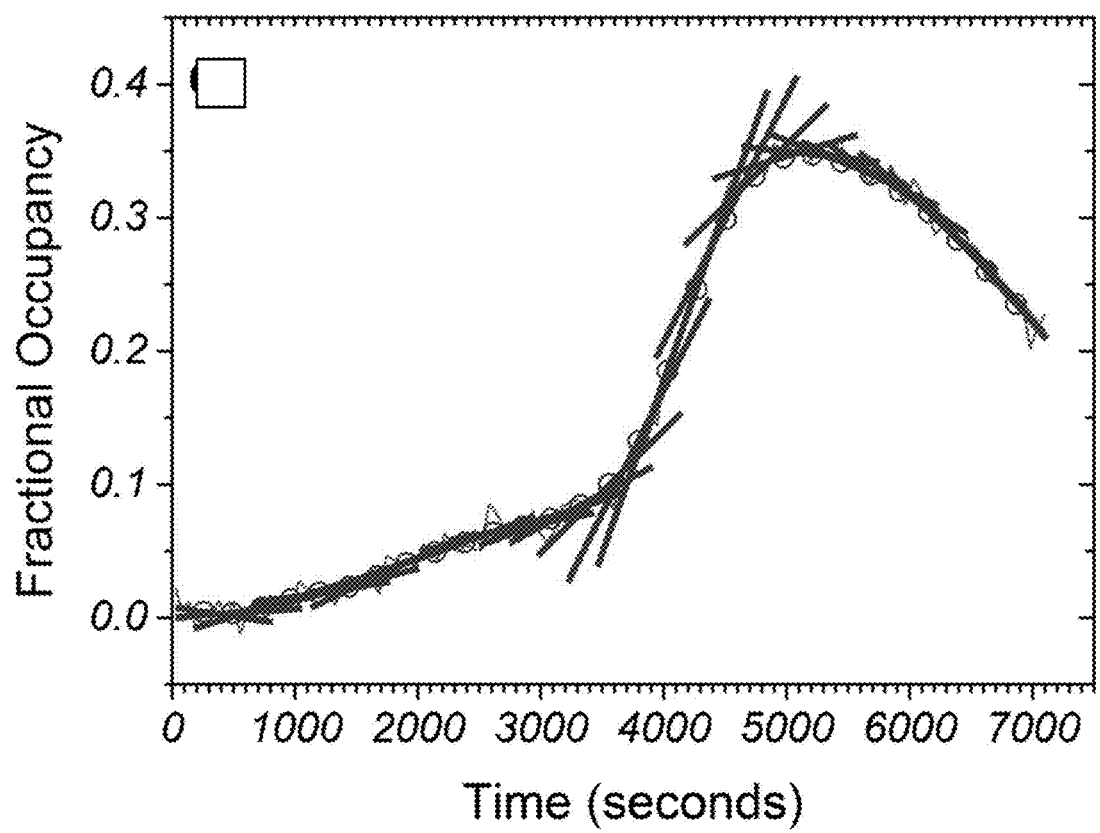
FIG. 14 is a graph of fractional occupancy vs time in determining extracellular concentrations from simulated data with local linear models fitted to the data.
Figure 15:
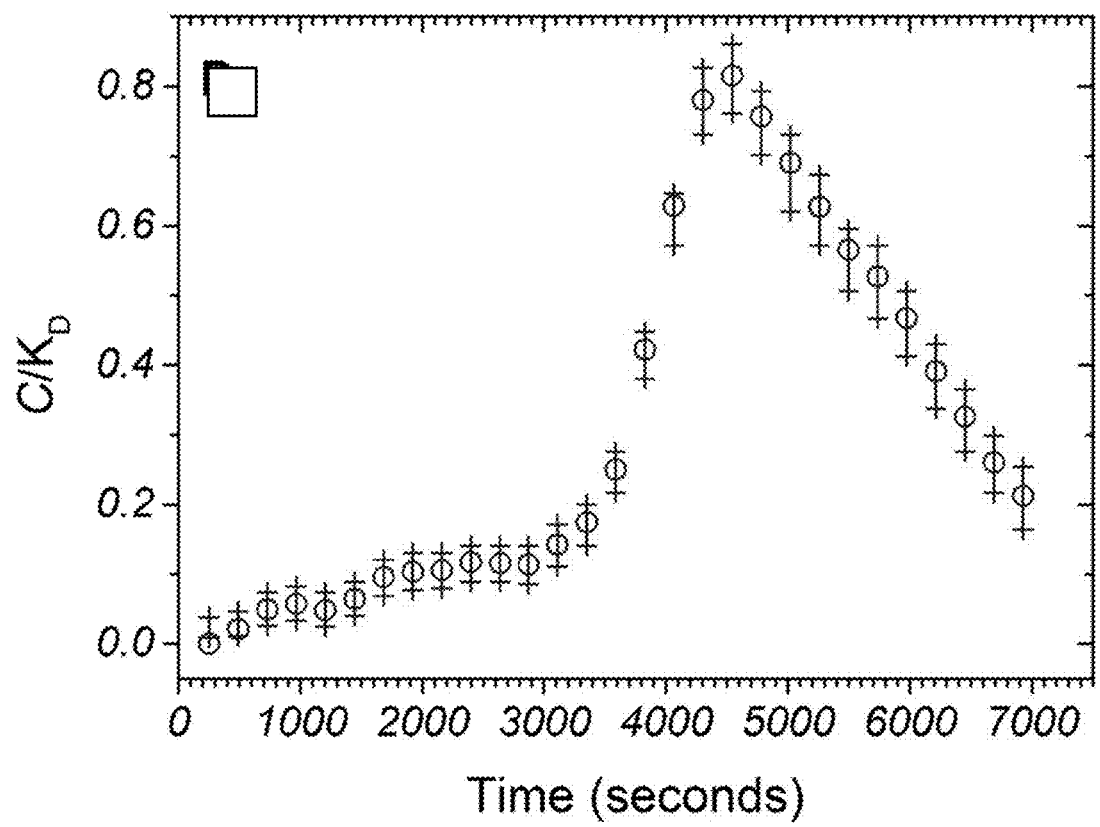
FIG. 15 is a graph of simulated extracellular concentration vs time.

With reference to FIGS. 12-15, determination of simulated extracellular concentration data is illustrated using the described method and system for receptor-ligand rate constants of $k_a=10^6$ $M^{-1}s^{-1}$, $k_d=10^{-3}s^{-1}$, and $K_D=1$ nM. In FIG. 12, a piece-wise function of three simulated time-dependent concentration scenarios is shown: a gradual increase; a sharp increase; and a sharp decline. In FIG. 13, time-dependent fractional occupancy was determined by solving the equation $\dot{f}=k_a C \cdot (1-f) - k_d f$, with added Gaussian noise typical of an experimental setup, is shown. In FIG. 14, local linear model fits to the fractional occupancy are shown. In this simulated example, the temporal filter is given a set width h of 270 seconds. In FIG. 15, simulated extracellular concentration $C/K_D$ is plotted over a plurality of times according to one aspect of the described methods and systems. The circles and error bars represent the determined mode of the concentration distribution divided by $K_D$ over a 5% to 95% confidence interval.

Because of the relatively high association rate of the receptor-ligand pair, the slow and rapid concentration increases are faithfully reproduced by the analysis with some curvature at the vertices due to the filter width. The decreasing concentration step is reproduced but with a time delay of approximately 250 seconds due to the relatively long receptor-ligand mean binding time, $1/k_d=1000$ seconds, which results in delayed sensitivity to sudden decreases in concentration.

b. Steady-State Secretions

Steady-state secretions of an analyte by several cells is quantified using the described methods and systems. Anti-c-myc-secreting hybridoma cells were introduced onto a LSPRi chip 12 with c-myc functionalized nanostructures 16. The density of the cells was adjusted so that the field of view included 2 to 3 cells. At a distance of 70 μm or more from the cells, the secreted antibody concentration fell below the array detection limit (approximately 100 pM) allowing for those arrays to be used as negative controls. By having such control arrays in the same field of view, global intensity variations, such as those due to focus drift, could be subtracted out from the signal of arrays adjacent to cells. At the end of each experiment, a saturating solution of commercial anti-c-myc antibodies was introduced in order to normalize the LSPRi intensity and calculate fractional occupancy. The kinetic rate constants used in the analysis were determined with a commercial SPR instrument (BioRad XPR36) using an identical surface functionalization protocol to that of the nanoplasmonic substrates: $k_a=2.68\times10^4$ $M^{-1}s^{-1}$, $k_d=4.75\times 10^{-5}$ $s^{-1}$, and $K_D=k_d/k_a=1.77$ nM.

Figure 16:
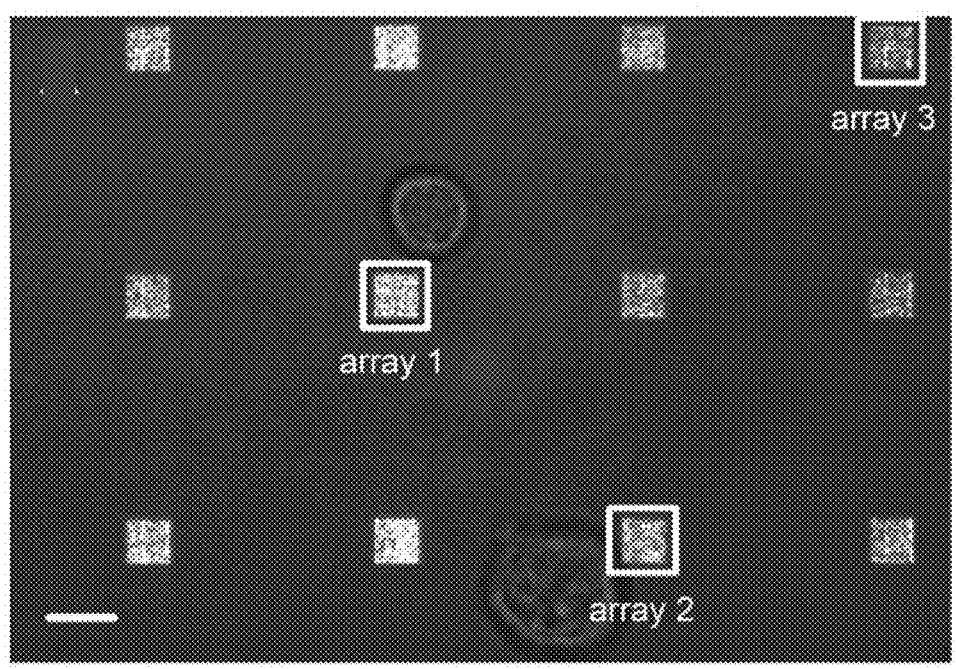
FIG. 16 is a photograph of an LSPR chip during the quantification of extracellular concentrations with steady-state secretions of a protein.

In FIG. 16, merged LSPRi and brightfield images showing two hybridoma cells among 12 arrays of plasmonic nanostructures is shown. The local arrays, labeled Array 1 and Array 2, were used to measure the antibody concentration near the upper and lower cells, respectively, while the remote array, labeled Array 3, was used as a control.

Figure 17:
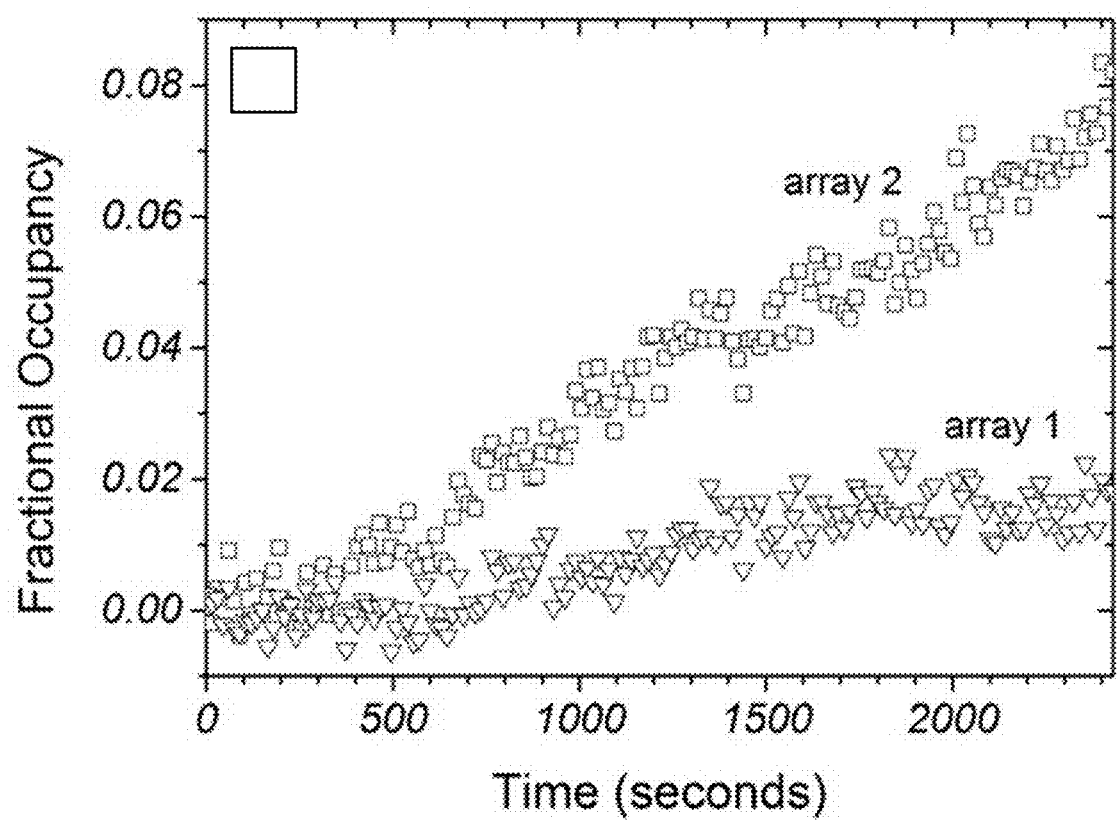
FIG. 17 is a graph of fractional occupancy vs time for two local arrays in the LSPR chip of FIG. 16.

In FIG. 17, the LSPRi-determined fractional occupancy is shown for array 1 and array 2 after subtracting control array data from array 3. The fractional occupancy data indicates that the lower cell was secreting at a higher rate than the upper cell.

Figure 18:
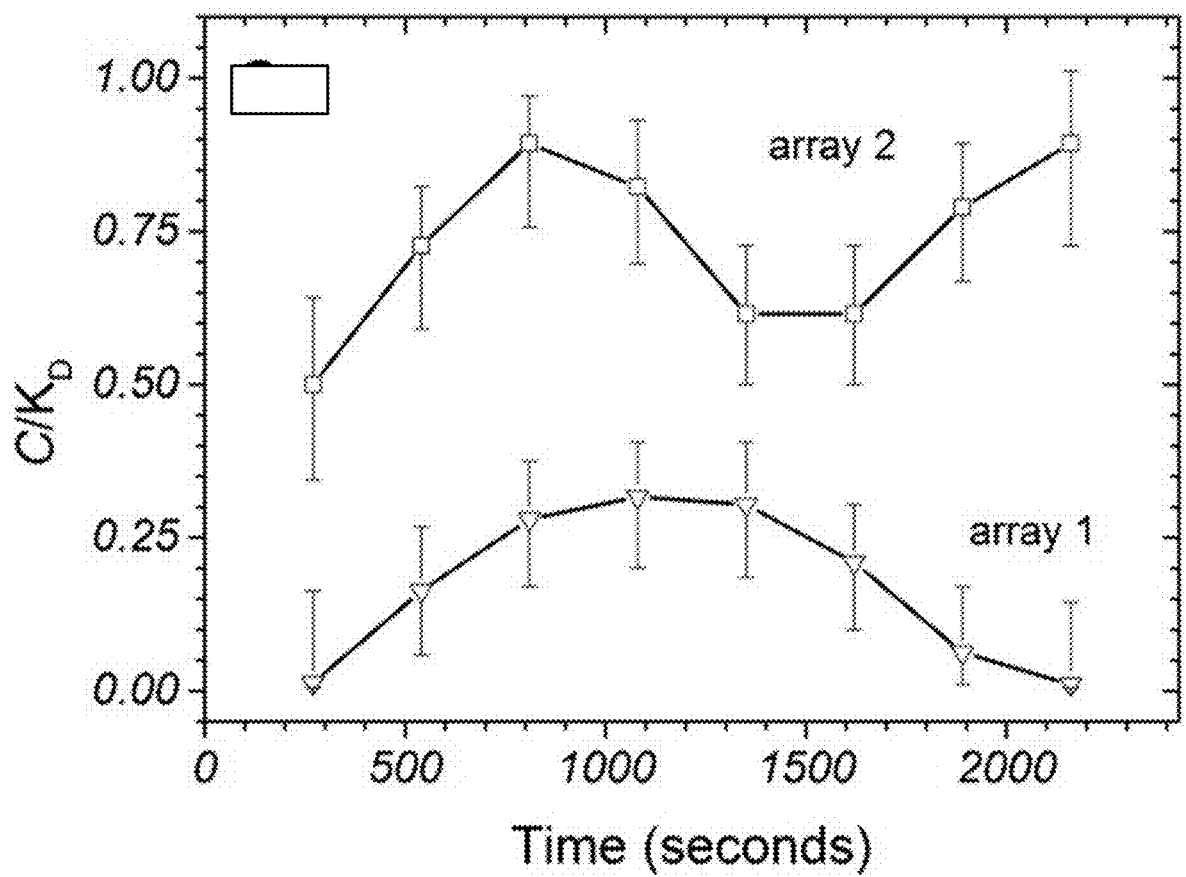
FIG. 18 is a graph of calculated extracellular concentration data for the local arrays of FIG. 16, after applying a temporal filter.

In FIG. 18, the calculated extracellular concentration data for arrays 1 and 2 are shown after applying a temporal filter with h=270 seconds. The symbols and error bars represent the mode of the concentration probability distribution divided by $K_D$ with a 5% to 95% confidence interval. The concentration data shows a constant concentration over 40 minutes, as expected for a steady-state secretion scenario, with an average concentration of 1.30 nM near the lower cell versus 230 pM for the upper cell.

c. Burst Secretions

Figure 19:
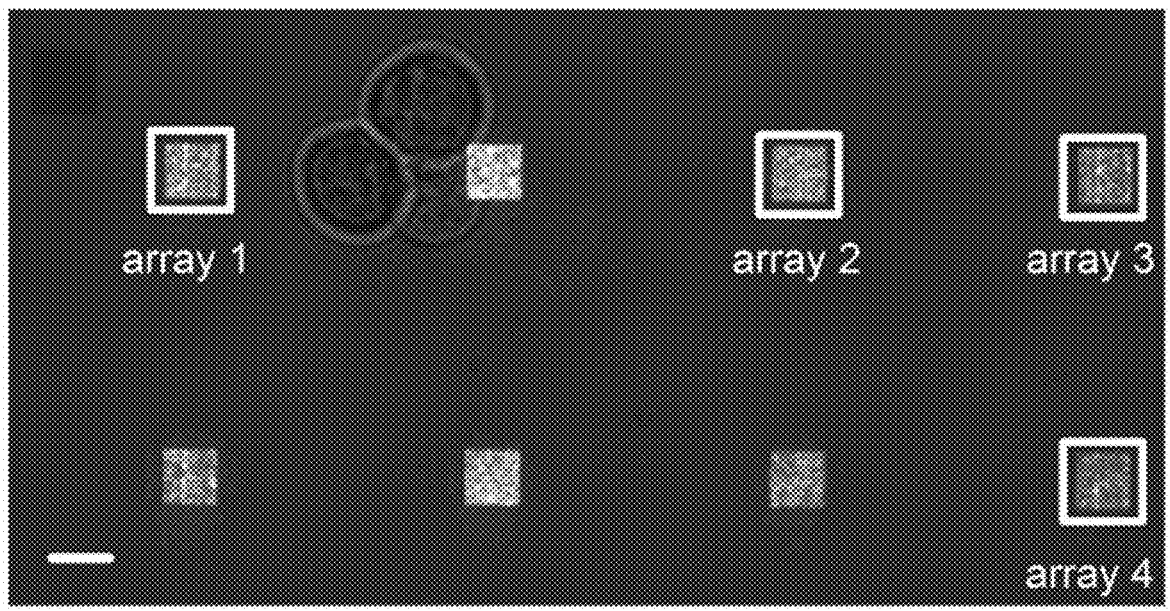
FIG. 19 is a photograph of an LSPR chip during the quantification of extracellular concentrations with burst secretions of a protein.
Figure 20:
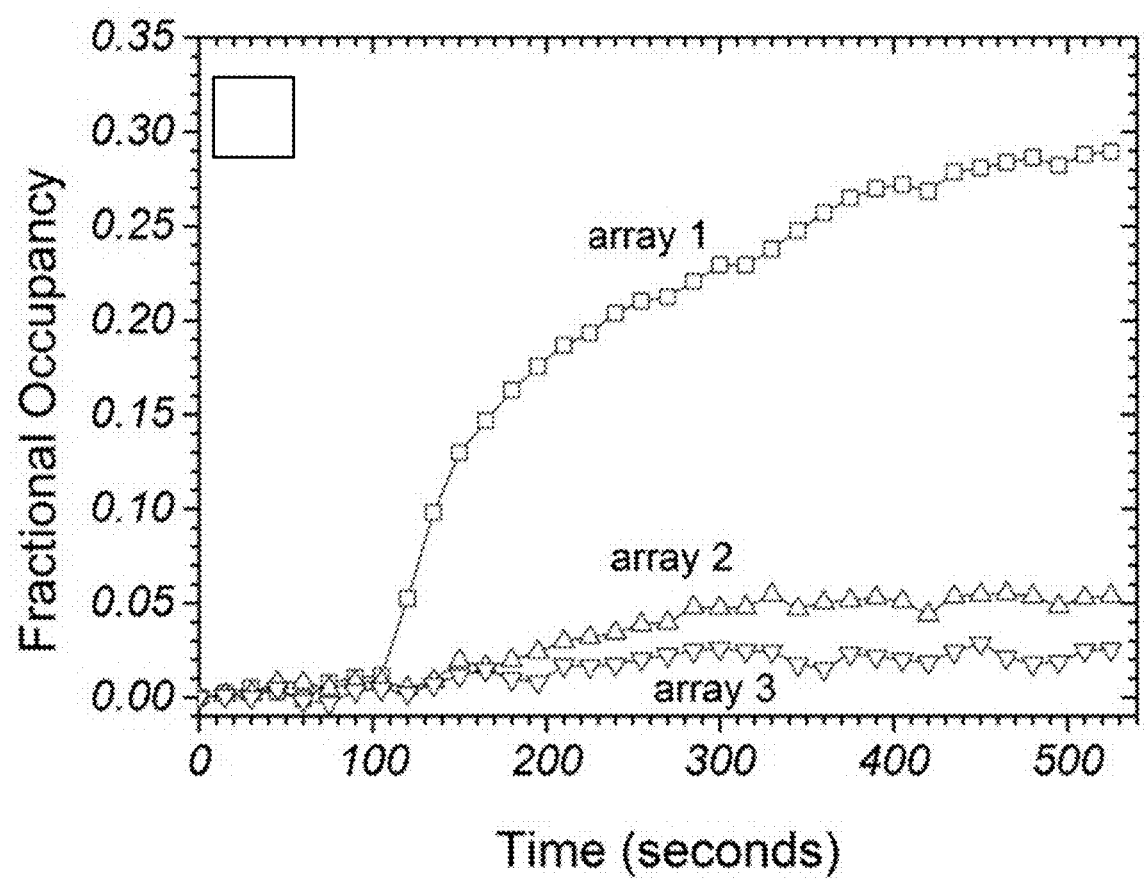
FIG. 20 is a graph of fractional occupancy vs time for the labeled arrays in the LSPR chip of FIG. 19.
Figure 21:
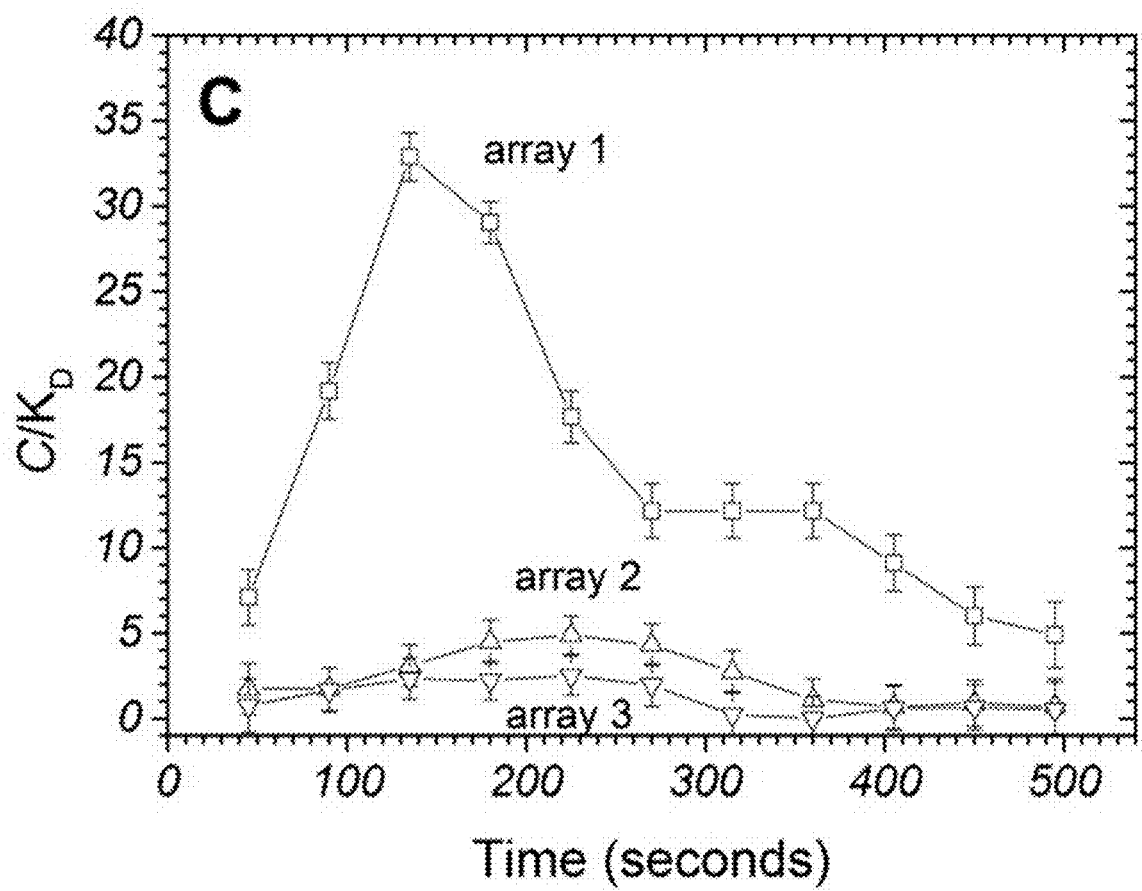
FIG. 21 is a graph of calculated extracellular concentration data for the labeled arrays of FIG. 19, after applying a temporal filter.

Anti-c-myc-secreting hybridoma cells were introduced onto a LSPRi chip with c-myc functionalized nanostructures, as for the steady-state secretion example. FIG. 19 shows merged LSPRi and brightfield images displaying a cluster of three hybridoma cells among 8 arrays. The arrays labeled array 1 and array 2 were used to measure the concentration at varying distances from the cell, while the array labeled array 3 was used as a control. FIG. 20 shows the LSPRi-determined fractional occupancy of the three labeled arrays. FIG. 21 shows the determined extracellular concentration for the three labeled arrays using a temporal filter with an h=45 s. The symbols and error bars represent the calculated mode of the concentration probability distribution divided by the $K_D$ at each time point with a 5% to 95% confidence interval.

The array labeled array 1 measured a rise in fractional occupancy that rose to 0.28 over the course of 2 minutes. This is in sharp contrast from the cells of FIG. 16 in which it took 40 minutes to reach a maximum fractional occupancy of 0.08. The concentration for array 1, located 24 μm from the center of the three cells, peaked at 56 nM within 2 minutes. The rapid increase and decrease in concentration was best resolved using a temporal filter with h=45 s. The secretion burst was also recorded by array 2 located 43 μm from the center of the three cells. The peak concentration at this array was 9 nM and time-delayed by 91 seconds from array 1, consistent with a burst of secreted antibodies diffusing outwardly from the three cells.

d. Signal to Noise Versus h Value

The methods and systems described herein for determining extracellular concentration data are adaptive in the sense that the width of the temporal filter, as described by h, can be adjusted to best accommodate the data. Longer h values enhance the signal to noise ratio (S/N) at the expense of reducing the temporal resolution.

Figure 22:
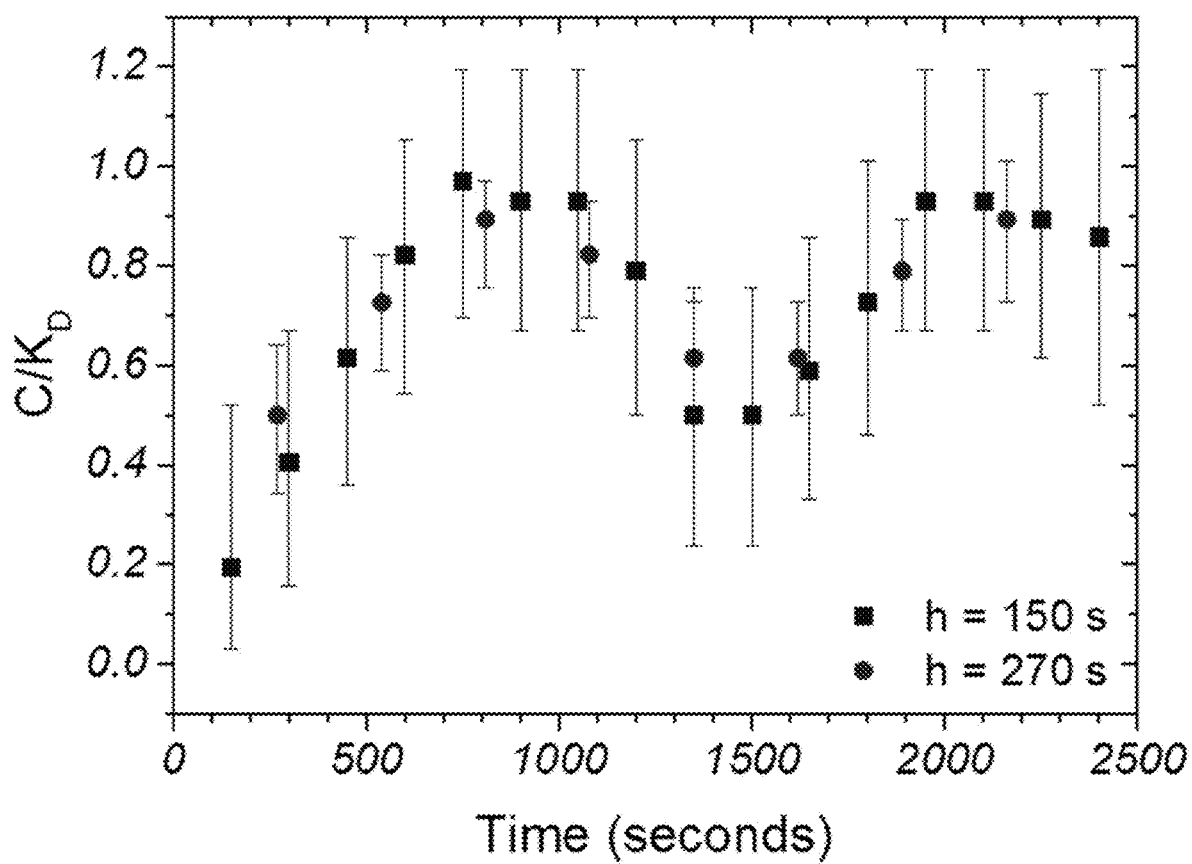
FIG. 22 is a graph of determined concentration for a local array of FIG. 16 two different time windows.

For example, with reference to FIG. 22, the determined concentration for array 2 in FIG. 16 was plotted for h=270 s and h=150 s. The concentration remains the same but the error is considerably less for the h=270 s data points. Because of the steady state nature of the secretion, the error bars overlapped for all the data and no temporal information was lost by using the longer h value.

Figure 23:
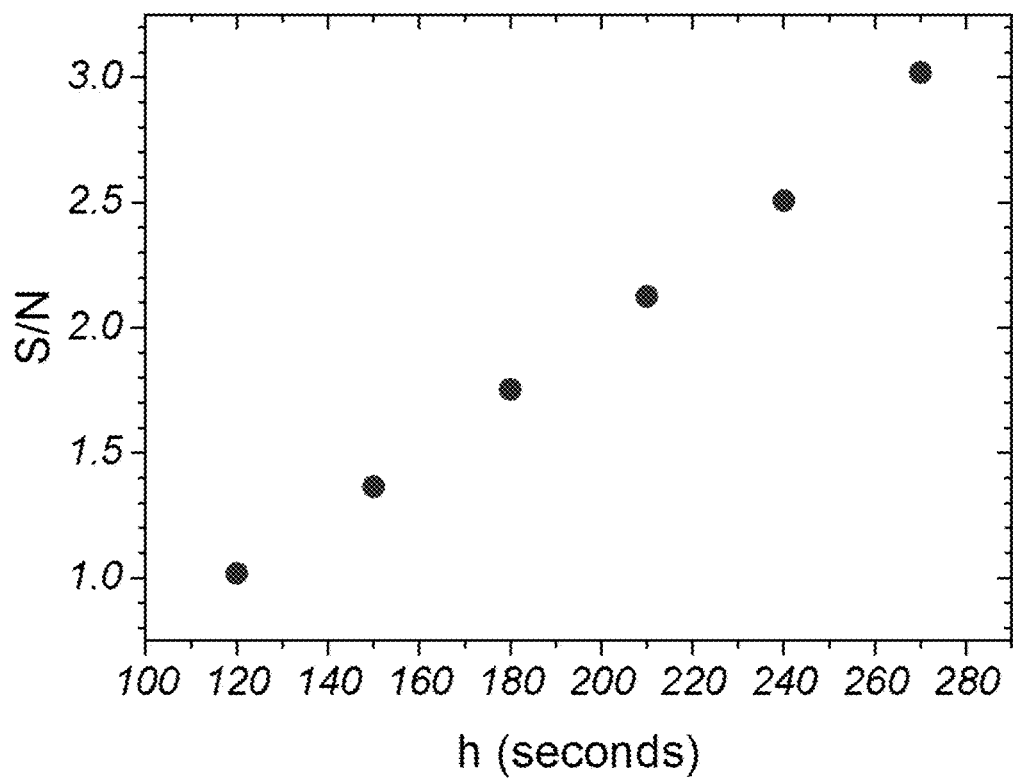
FIG. 23 is a graph of the signal to noise ratio with varying time window.

With reference to FIG. 23, the effect of varying h on the S/N ratio is shown for the determined concentrations of array 2 from FIG. 16. In general, the S/N increases linearly with increasing h values.

A comparison of the h values used in FIGS. 18 and 21 highlights the value of taking an adaptive approach to the determination of extracellular concentration data. The data from FIG. 16, being steady state in nature, can accommodate the longer h value without loss of temporal information and take advantage of the improved signal-to-noise ratio. In FIG. 21, however, the signal-to-noise is reduced by the shorter h value but the peaks in time are readily resolved. The dynamic range of the nanoplasmonic sensors is also highlighted by these two figures, in which the 56 nM peak of FIG. 21 is 244-fold greater than the concentration measured at the lower cell of FIG. 16. In general, the optimally designed sensor will have a $K_D$ value centered within the range of possible secretions.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:

1. An imaging method for determining concentrations of an analyte, the method comprising:
    forming at least one array of functionalized plasmonic nanostructures on a localized surface plasmon resonance imaging (LSPRi) chip;
        contacting the at least one array with a fluid comprising an analyte;
        illuminating the at least one array with a visible light source causing the nanostructures to emit sensor data;
        imaging the illuminated plasmonic nanostructures of the at least one array with a camera for each of a plurality of times;
        measuring brightness intensity data of the nanostructures for each of the plurality of times using camera imagery;
        determining fractional occupancy data for the nanostructures using the brightness intensity data measured by the camera for each of the plurality of times since there is a linear relationship between intensity data from the camera and fractional occupancy; and
        determining concentration data of the analyte based on the fractional occupancy data using the law of mass action.

2. The method of claim 1, wherein the method is performed without the use of a spectrometer.

3. The method of claim 1, wherein sensor data is received from a camera positioned to receive emissions from at least one of the arrays.

4. The method of claim 1, wherein the fractional occupancy data comprises a fractional occupancy ($\mu_i$) and standard deviation ($\sigma_i$) determined for each of the plurality of times.

5. The method of claim 1, wherein the determining of the extracellular concentration data of the analyte comprises:
    subsampling the fractional occupancy data using a temporal filter over the plurality of times; and
    calculating time-derivative fractional occupancy data.

6. The method of claim 5, wherein the temporal filter has a center at a time (t) and a width (h) for each instance of subsampling over the plurality of times.

7. The method of claim 6, wherein the temporal filter assigns a weight (w) to the fractional occupancy data within each instance of subsampling over the plurality of times, based on the center and the width of the temporal filter of that subsample.

8. The method of claim 7, wherein the temporal filter assigns the weight (w) based on a symmetric, positive, location-scale function selected from a Gaussian profile, a Lorentzian profile, and an Epanechnikov profile.

9. The method of claim 5, wherein the determining of the extracellular concentration data of the analyte further comprises:
    calculating at least one local linear models with a model fractional occupancy (f) and a model time-derivative fractional occupancy (ḟ) for each instance of subsampling of the fractional occupancy data; and
    determining at least one probability distributions for each set of local linear models at each instance of subsampling of the fractional occupancy data.

10. The method of claim 9, wherein the probability distributions are determined as a negative log likelihood that the local linear models will fit the subsampled fractional occupancy data.

11. The method of claim 9, wherein the probability distributions are determined as a bivariate normal distribution that is exact for linear models.

12. The method of claim 9, wherein the determining of the concentration data of the analyte further comprises calculating a probability of a concentration of the analyte, based on the probability distributions for each of instances of subsampling.

13. The method of claim 1, further comprising determining movement of the analyte in the fluid from the concentration data by mapping the concentration data of the analyte for each of the at least one array of nanostructures over the plurality of times.

14. The method of claim 1, wherein the method further comprises calibrating the LSPRi chip by saturating the nanostructures with a known concentration of the analyte.

* * * * *